US008163489B2

(12) United States Patent
Murray et al.

(10) Patent No.: US 8,163,489 B2
(45) Date of Patent: Apr. 24, 2012

(54) METHOD FOR A CONTINUOUS RAPID THERMAL CYCLE SYSTEM

(75) Inventors: Elizabeth Murray, Huntington, WV (US); Derek Allen Gregg, Huntington, WV (US); Michael Louis Norton, Huntington, WV (US); Justin Thomas Swick, Huntington, WV (US); William Ian Towler, Dublin, OH (US)

(73) Assignee: Vandalia Research, Inc., Huntingdon, WV (US)

( * ) Notice: Subject to any disclaimer, the term of this patent is extended or adjusted under 35 U.S.C. 154(b) by 30 days.

(21) Appl. No.: 12/384,554

(22) Filed: Apr. 6, 2009

(65) Prior Publication Data
US 2010/0267091 A1 Oct. 21, 2010

Related U.S. Application Data

(63) Continuation of application No. PCT/US2007/021328, filed on Oct. 4, 2007.

(60) Provisional application No. 60/850,103, filed on Oct. 6, 2006.

(51) Int. Cl.
*C12Q 1/68* (2006.01)
*C12P 19/34* (2006.01)
(52) U.S. Cl. .......... 435/6.12; 435/6.1; 435/6.11
(58) Field of Classification Search .......... None
See application file for complete search history.

(56) References Cited

U.S. PATENT DOCUMENTS

| 5,176,203 A | 1/1993 | Larzul |
| 5,270,183 A | 12/1993 | Corbett |
| 5,508,197 A | 4/1996 | Hansen |
| 5,736,314 A | 4/1998 | Hayes et al. |
| 5,849,208 A | 12/1998 | Hayes |
| 6,033,880 A | 3/2000 | Haff et al. |
| 6,132,996 A | 10/2000 | Hunicke-Smith |
| 6,613,560 B1 | 9/2003 | Tso et al. |
| 6,632,653 B1 | 10/2003 | Astle |
| 6,709,692 B2 * | 3/2004 | Sudor ............ 427/2.1 |
| 7,015,030 B1 | 3/2006 | Fouillet et al. |
| 7,133,726 B1 | 11/2006 | Atwood |
| 2003/0017551 A1 * | 1/2003 | Parthasarathy et al. ...... 435/91.1 |
| 2008/0038813 A1 | 2/2008 | Chen |
| 2009/0057147 A1 | 3/2009 | Kayyem |
| 2009/0325234 A1 | 12/2009 | Gregg et al. |

FOREIGN PATENT DOCUMENTS

| WO | WO 98/16313 | 4/1998 |
| WO | WO 2005075683 A1 * | 8/2005 |

OTHER PUBLICATIONS

Kim et al., "Fabrication and characterization of a PDMS-glass hybrid continuous-flow PCR chip," Biochemical Engineering Journal, 2006, pp. 91-97.*
International Search Report of WO 2008/045288, Apr. 17, 2008, Vandalia Research, Inc.
Curico, M. and Roeraade, J. (2003, published on web 2002) Continuous Segmented Flow Polymerase Chain Reaction for High-Throughput Miniaturized DNA Amplification, Anal. Chem. 75, 1-7.

* cited by examiner

*Primary Examiner* — Young J Kim
(74) *Attorney, Agent, or Firm* — Geoffrey M. Karny

(57) ABSTRACT

Disclosed herein is an efficient, high speed production scale synthesis method for high molecular weight organic substances, such as DNA. The invention includes a method of conducting a polymerase chain reaction which comprises transporting a liquid through polymeric tubing disposed through a first reaction cycle region and at least a second reaction cycle region, each of which regions comprises at least a first and a second temperature zone, the temperature in each zone of said at least second region being substantially identical to the corresponding first and second zones in said first region, wherein said liquid is an aqueous solution comprising polymerase chain reaction reactants and a surface absorbing polymer.

17 Claims, 17 Drawing Sheets

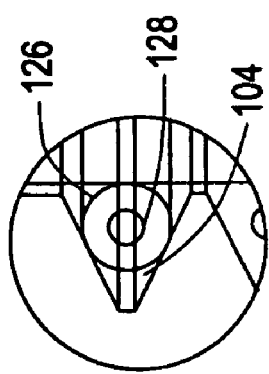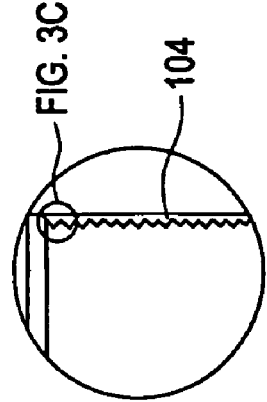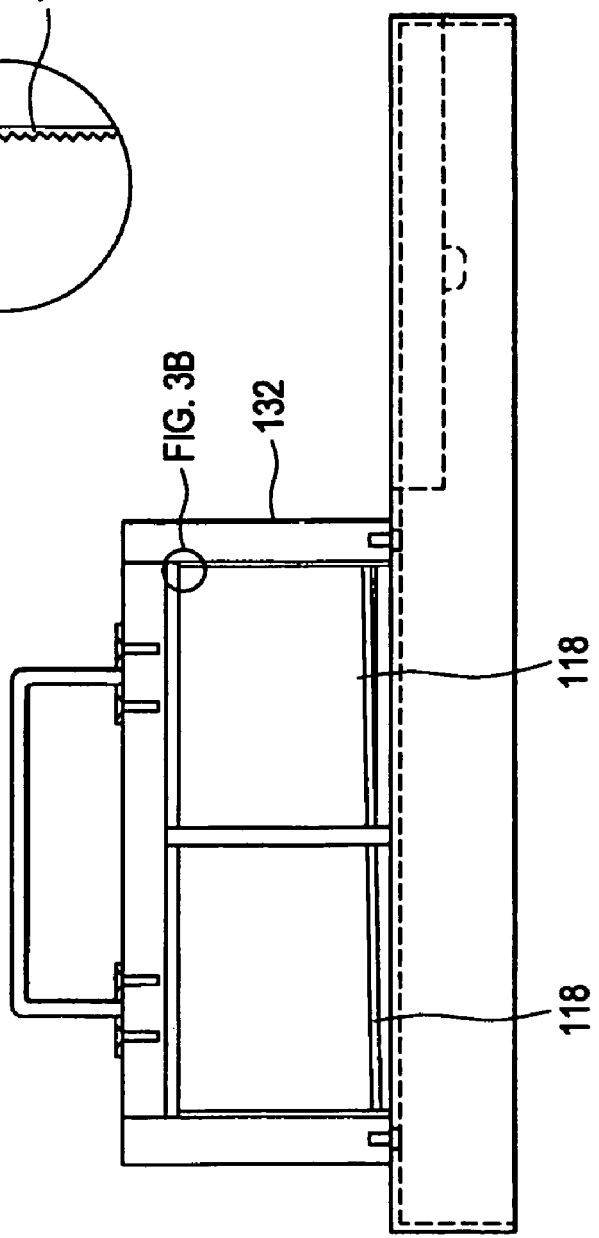

METHOD FOR A CONTINUOUS RAPID THERMAL CYCLE SYSTEM

RELATED APPLICATION

This application is a continuation of, and claims the benefit under 35 U.S.C. §§120 and 365(c) of, International Patent Application No. PCT/US2007/021328, filed Oct. 4, 2007, which claims priority to, and the benefit of, U.S. Provisional Patent Application No. 60/850,103 filed Oct. 6, 2006. The contents of Provisional Patent Application No. 60/850,103 are incorporated by reference herein in their entirety.

INTRODUCTION

Polymerase chain reaction (PCR) is a three step process normally designed for diagnostic, identification or forensic purposes. In the first step, DNA, or a similar molecule, is denatured, also referred to as split, separated or unwound at a temperature of about 94-96° Centigrade (C). In the second step the strands produced in the first step are annealed, also known as primed or hybridized with the polymerase initiator or primer reactant at a temperature of about 55-60° C. In the third step, the thus-primed single strand of DNA is allowed to synthesize a replicate DNA via extension of the primer as individual nucleotide bases are added at about 70-73° C. Newer PCR processes also may use a two temperature zone operation. Newer PCR processes also may use a two temperature zone operation.

Devices for PCR operate generally by a batch method where a plate of wells with individual aliquots of reactants is physically moved from one temperature environment to another to complete the cycle. Alternatively, a stream of cassettes, microbottles, tubes or other vessels is passed through a fixed series of ovens. Alternatively the tubes are placed in a block which is heated and cooled to change the temperature of the liquid reactant contained with the cassettes, microbottles, tubes or other vessels within the block.

In more detail, PCR is widely used by research professionals around the world as a means to amplify small strands of DNA in a quantity sufficient for detection and identification. Typically, PCR is performed using automated thermal cyclers that alternately heat and cool numerous small tubes containing the PCR reaction mixture. Such a process uses a static reactor having discrete, confined spaces in which the reaction occurs when exposed to different temperatures in a repetitive sequence. The process is time intensive, labor intensive, and inefficient, as the tubes must be individually filled with reactants, closed, processed through the automatic cycler, opened, and finally drained of the reaction product that contains the desired amplified DNA.

Accordingly, continuous thermal cyclers were developed to eliminate the need for using a multitude of small tubes to amplify DNA via PCR by using a dynamic reactor. Rather than using small tubes, continuous thermal cyclers use a constant or continuous stream of fluid repetitively passed through different temperature zones to amplify DNA. One example of a continuous thermal cycler is disclosed in U.S. Pat. No. 5,270,183 issued Dec. 14, 1993, to Corbett et al. Corbett et al. disclosed a device and method for DNA amplification in which a PCR reaction mixture is injected into a carrier fluid with which the PCR reaction mixture is immiscible, and the carrier fluid then passes through a plurality of temperature zones to facilitate DNA amplification within the PCR reaction mixture. Thus, individual reaction mixtures are separated by a volume of carrier fluid. The function of this device is to accelerate the processing of a multitude of different DNA strands contained in discrete pockets or plugs, hence the need for a carrier fluid that is immiscible with the PCR reaction mixture that acts to separate the different DNA strands. This device is not designed to produce mass quantities of DNA.

Moreover, the Corbett et al. device is not designed to be easily and quickly adaptable to different PCR reaction requirements. For example, the preferred arrangement for passing the carrier fluid through the temperature zones is to wrap tubing conveying the carrier fluid around separate cylinders maintained at different temperatures. Modifying the device for different reaction conditions therefore requires re-wrapping the tubing around one or more of the cylinders a different number of times, unwrapping the tubing around one or more of the cylinders to replace one or more of the cylinders with different cylinders, re-routing the tubing around the cylinders in different orders, or another such labor-intensive procedure. Additionally, efficiency and fine temperature control is reduced as the reaction mixture pockets pass from one cylinder to the next and thermal energy is unintentionally lost or gained at such "gaps."

Another example of a continuous thermal cycler is disclosed in Curico, M. and Roeraade, J. (2003, published on web 2002) Continuous Segmented Flow Polymerase Chain Reaction for High-Throughput Miniaturized DNA Amplification, Anal. Chem. 75, 1-7. This device similarly is designed for numerous small sample mixtures separated by an immiscible fluid. Rather than using separate cylinders as different temperature zones as in the Corbett et al. device; however, this device uses separate thermally controlled water baths as temperature zones. This device is not designed for easy modification for providing a number of different reaction conditions, as additional water baths would have to be prepared and added for such modification. Use of this device also entails adding, checking, and draining water from the baths on periodic basis, as well as cleaning of the water bath containers.

U.S. Pat. No. 5,508,197 issued Apr. 16, 1996 to Hansen teaches a PCR apparatuses with multi-well plates of 96, 192 and 384 well formats together with plate holder stations.

U.S. Pat. No. 5,849,208 issued Dec. 15, 1998 to Hayes describes a plurality of reaction chambers and a plurality of analysis chambers wherein a cassette is used to maintain the biological material for both the PCR and subsequent analysis.

U.S. Pat. No. 6,632,653 issued Oct. 14, 2003 to Astle teaches a PCR apparatus with an indexing step to index patterns of reagent wells on a continuous basis with unique temperature changes.

U.S. Pat. No. 6,709,692 issued Mar. 23, 2004 to Sudor describes a treatment of surfaces using surface treatment polymers as well as methods for performing fluid operations, including PCR, on such surfaces. Surfaces include those of apparati such as test tubes, multi-plate wells, pipettes and capillaries.

U.S. Pat. No. 7,133,726 issued Nov. 7, 2006 to Atwood teaches an assembly which cycles samples through a series of temperature excursions, a cover and a computer to control the process.

SUMMARY OF THE INVENTION

A method of conducting a polymerase chain reaction which comprises transporting a liquid containing polymerase chain reaction reactants through polymeric tubing disposed through a first reaction cycle region and at least a second reaction cycle region, each of which regions comprises a first and second, or a first, a second and a third temperature zone, the temperature in each zone of said second region is substantially identical to the corresponding zones in said first region, wherein said liquid is an aqueous solution comprising polymerase chain reaction reactants and a surface absorbing polymer.

There is a need for a continuous thermal cycler that is designed to mass produce DNA strands, that is easily adaptable to different PCR reaction requirements, and that is efficient in operation.

A method for a continuous thermal cycle system capable of the bulk production of DNA strands that is efficient, scalable, easily adaptable to different PCR reaction requirements, and is relatively inexpensive to produce is provided. An embodiment of the present invention has a plurality of temperature-controlled sectors within a temperature control body, thereby resulting in a plurality of temperature zones. A fluid preferably flows continuously through or along the apparatus via a path, and thereby through or along the different temperature zones.

A preferred embodiment of the present invention is particularly suited for amplification of DNA fragments quickly, easily, and in large quantities. Mass production of DNA at rates much greater than conventional DNA production rates is thereby effectively achieved using the present invention. Low manufacturing costs and enhanced scalability of the present invention permit relatively inexpensive, continuous amplification of DNA in bulk quantities. In particular, a preferred embodiment of the present invention comprises a single cylindrical temperature control body having twelve pie-shaped or wedge-shaped sectors, each sector having a means for obtaining a desired temperature, and each sector separated from other sectors by a thermal barrier. A grooved channel circles or spirals around the exterior surface of the temperature control body, and a length of tubing placed in or on the channel conveys DNA amplification reactants cyclically from one sector o subsequent sectors. The reactants are thereby exposed to different temperature zones in a cyclical fashion, ultimately resulting in the amplification of the DNA. A means for moving the reactants establishes the flow rate of the reactants through the length of tubing to optimize the amplification via PCR based upon the characteristics of the specific reactants. Any number of sectors may be incorporated into the temperature control body by simply dividing it into additional sections or reducing the number of sectors. Also, further adaptability can be incorporated into the temperature control body by adding layered sectors and/or using a temperature control body having a shape other than a cylinder, e.g. having an elliptical cross-section.

BRIEF DESCRIPTION OF THE FIGURES

The present invention is described with reference to the accompanying drawings. In the drawings, like reference numbers indicated identical or functionally similar elements.

FIG. 3A is an elevation view of an alternate embodiment of the thermal cycle system of the present invention.

FIG. 3B is an expanded view of a portion of an exterior surface of the thermal cycle system of FIG. 3A.

FIG. 3C is an expanded view of a portion of a channel of the thermal cycle system of FIG. 3A.

DETAILED DESCRIPTION OF THE INVENTION

Figure 1:
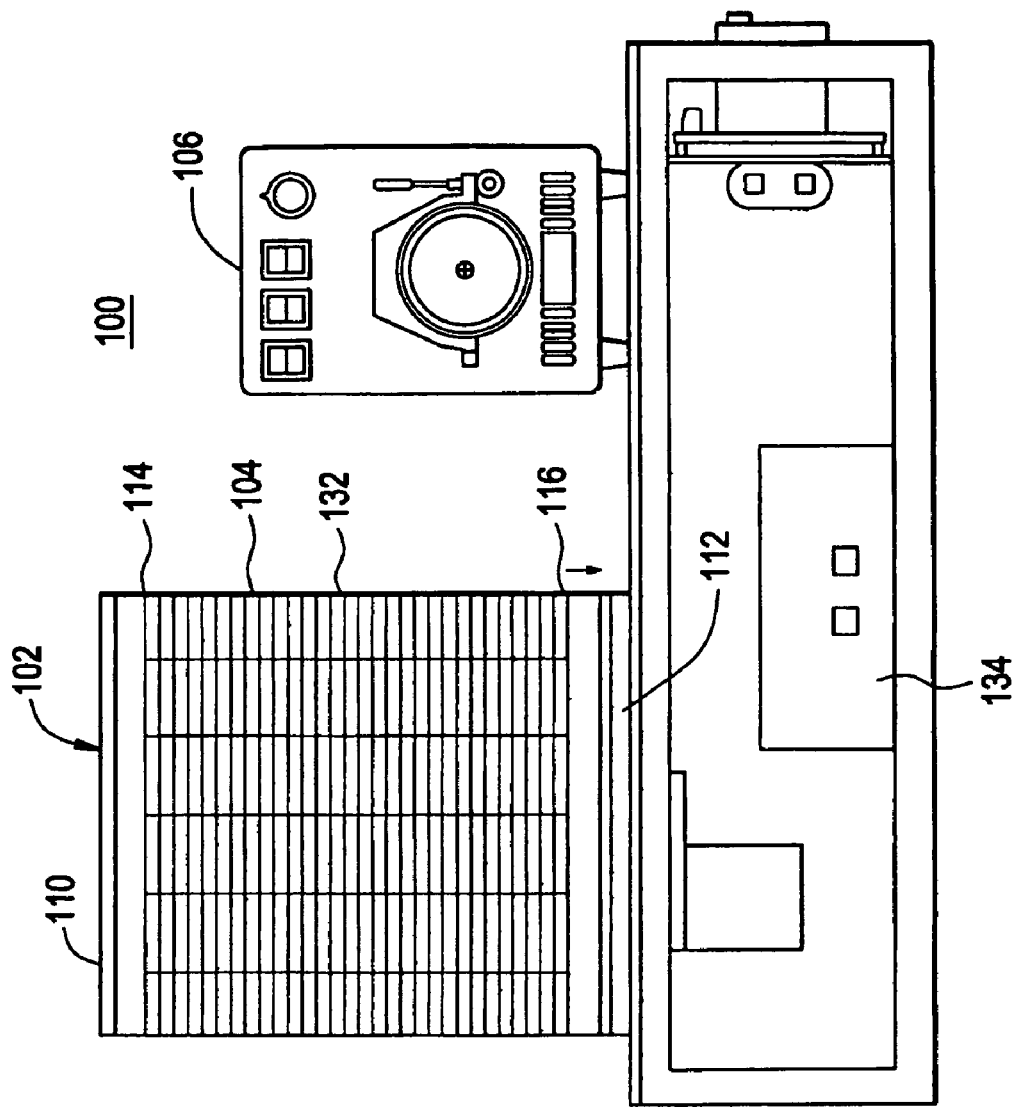
FIG. 1 is an elevation view of an embodiment of a thermal cycle system of the present invention.
Figure 2:
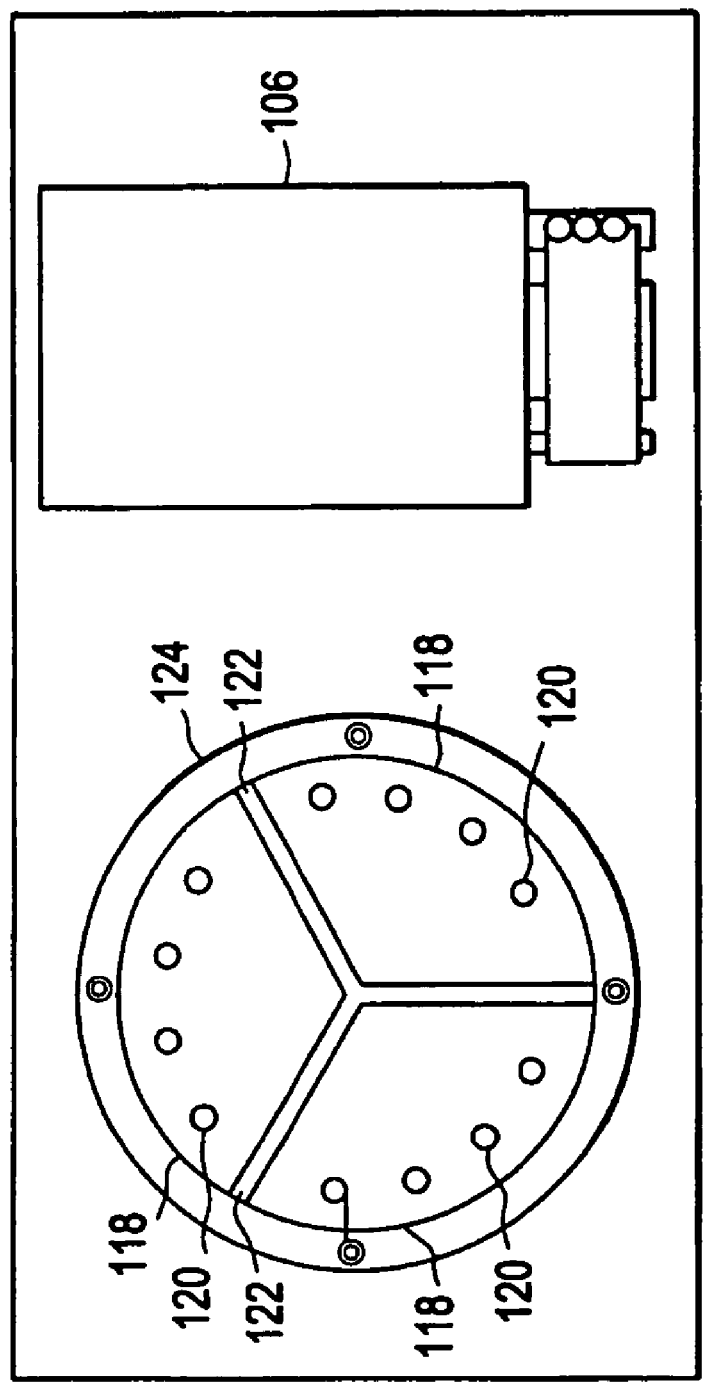
FIG. 2 is a plan view of the thermal cycle system of FIG. 1.
Figure 4:
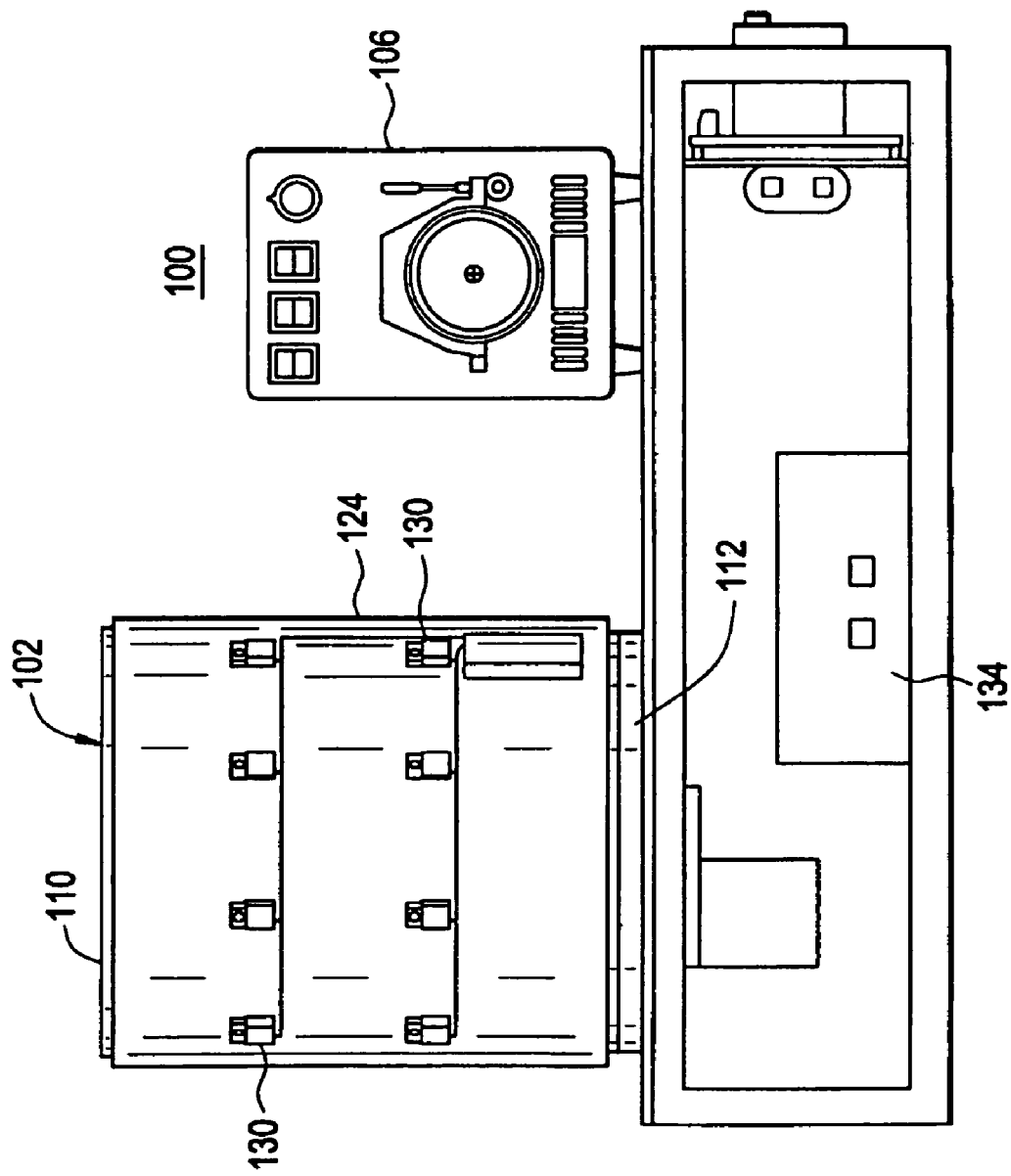
FIG. 4 is an elevation view of the thermal cycle system of FIG. 1 showing an insulating layer substantially surrounding the temperature control body.
Figure 5:
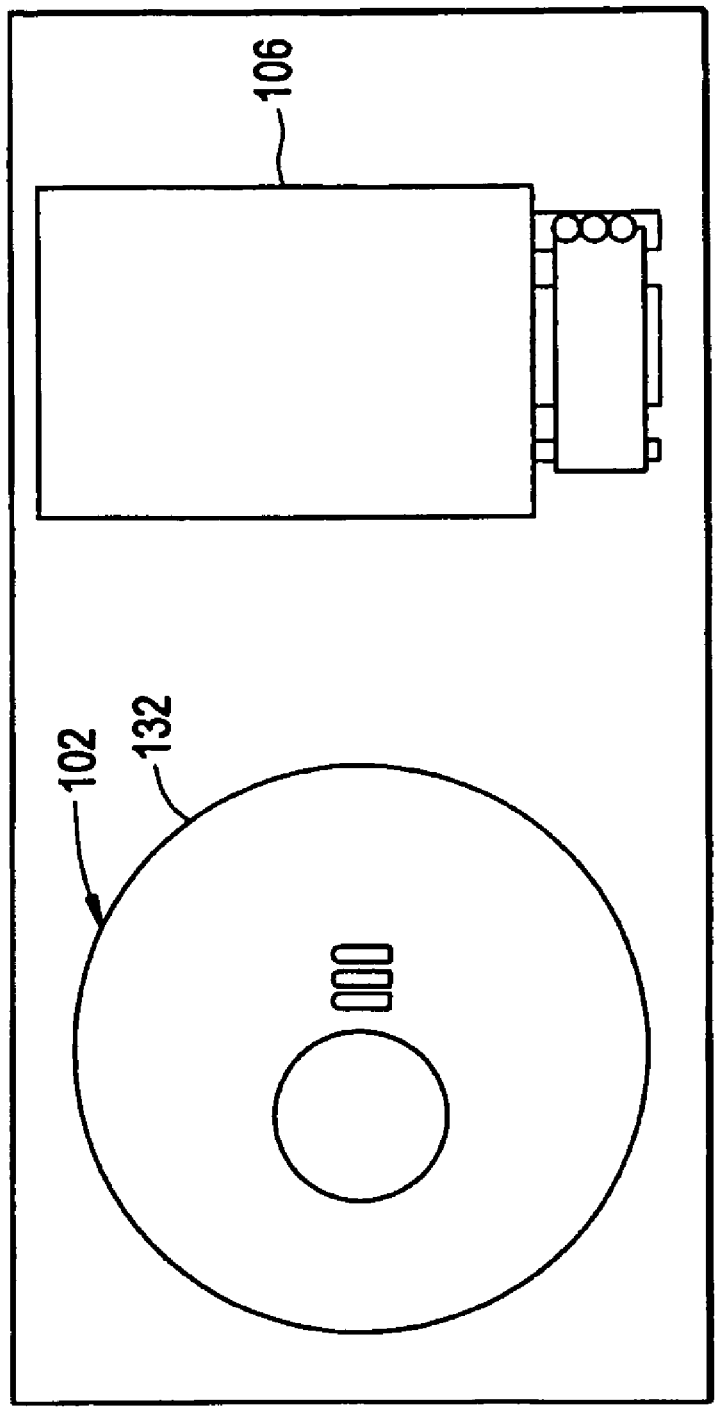
FIG. 5 is a top plan view of the thermal cycle system of FIG. 1.
Figure 6:
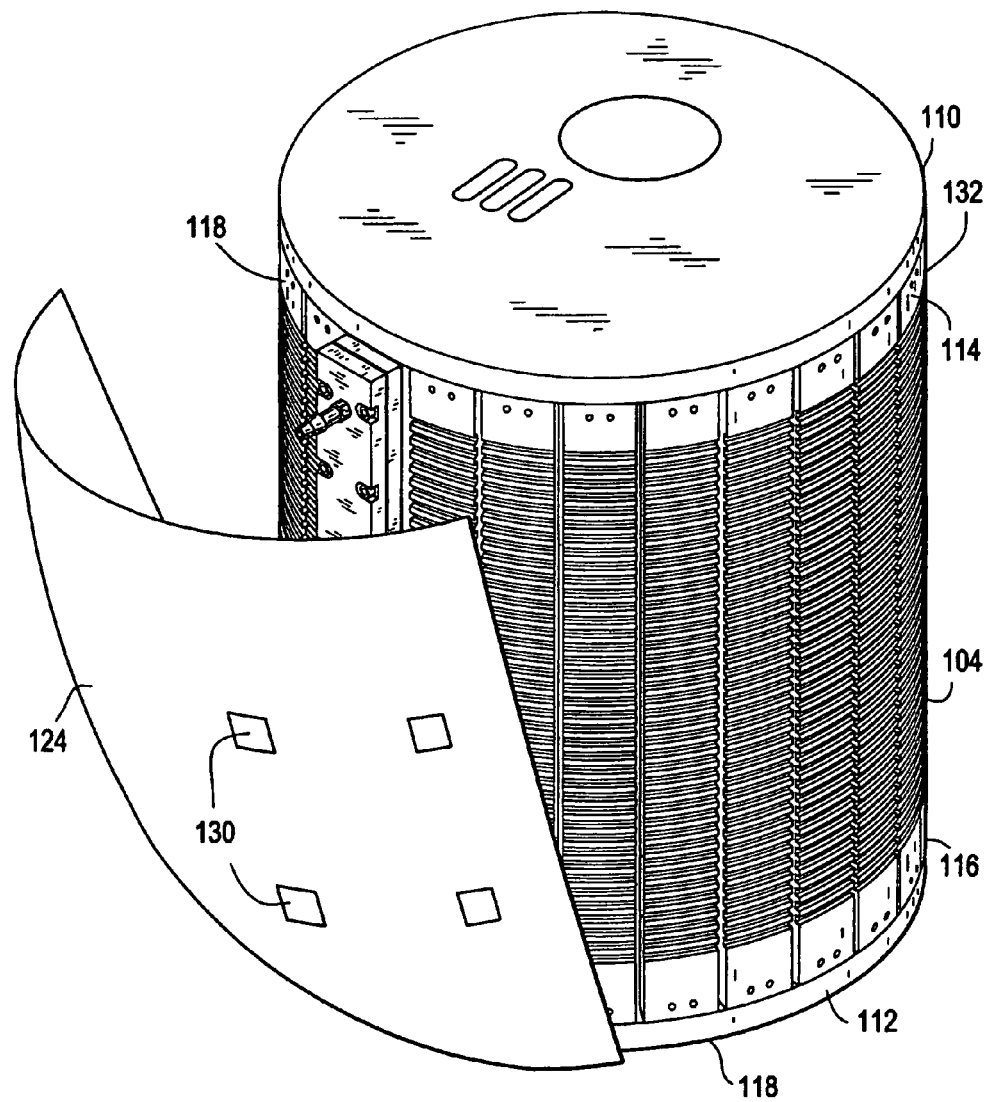
FIG. 6 is a perspective view of a temperature control body of the thermal cycle system of FIG. 1 showing a portion of an insulating layer.
Figure 7:
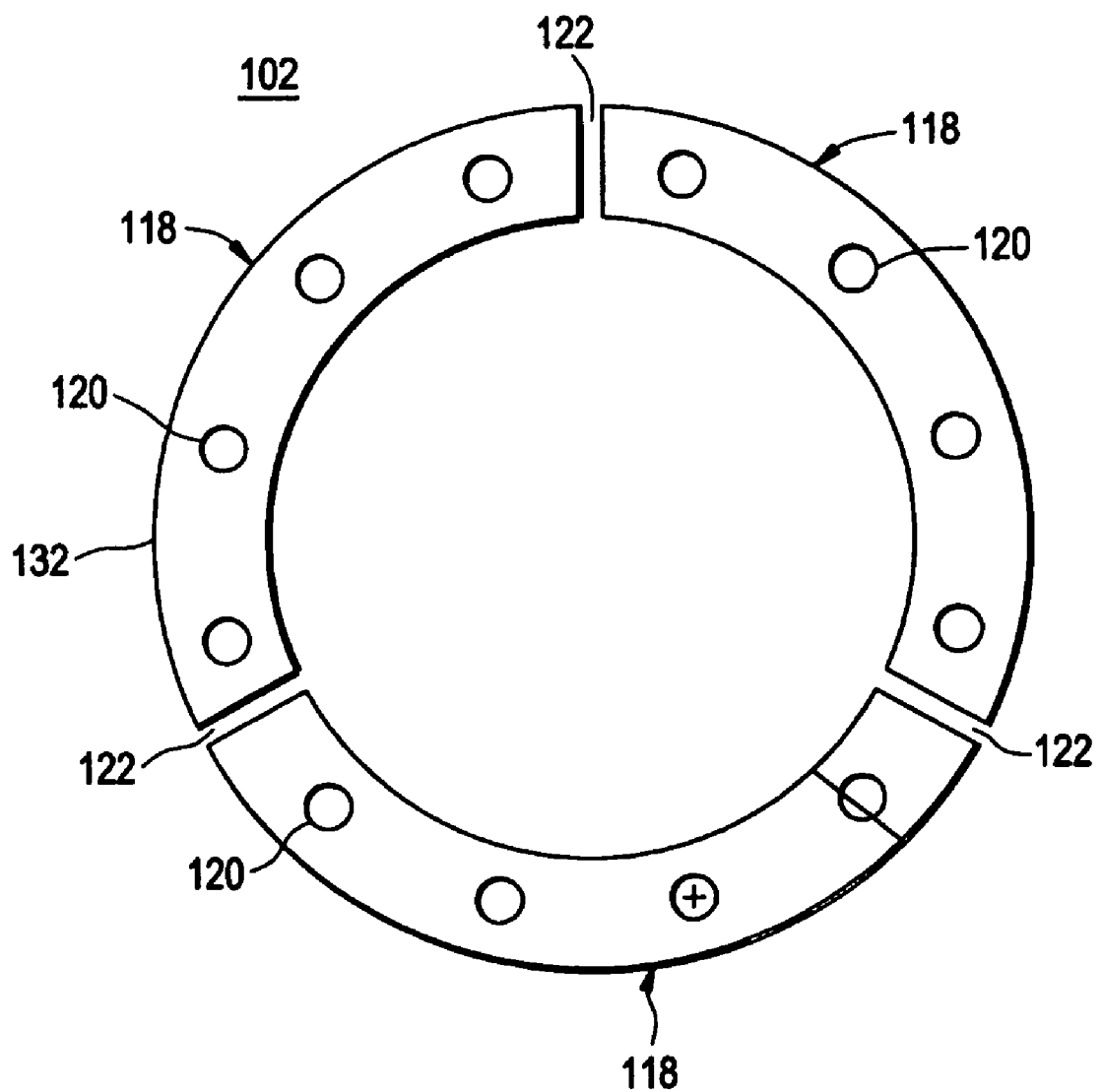
FIG. 7 is a top plan view of a temperature control body of the thermal cycle system of FIG. 1.
Figure 8:
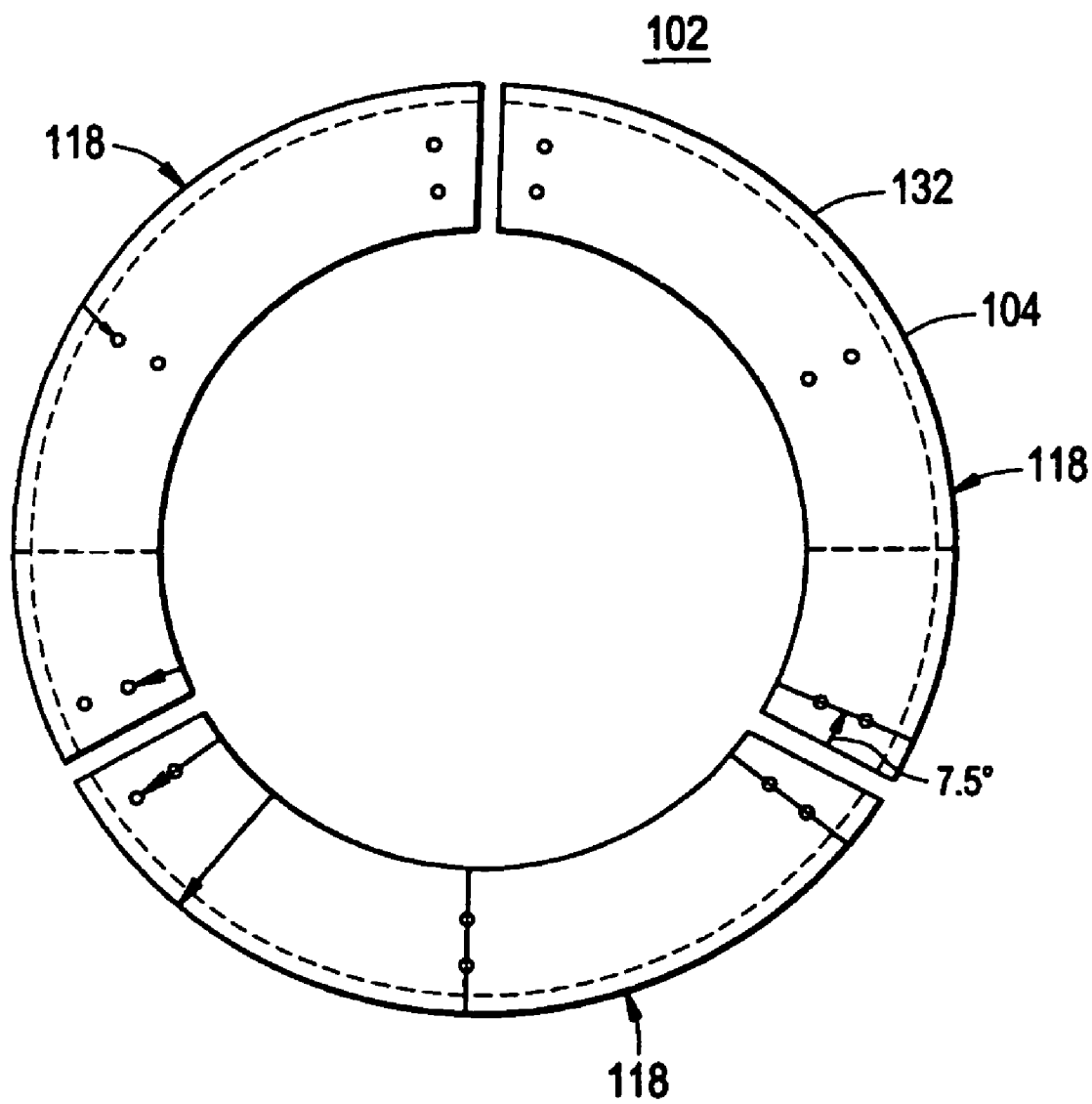
FIG. 8 is a bottom plan view of a temperature control body of the thermal cycle system of FIG. 1.
Figure 9:
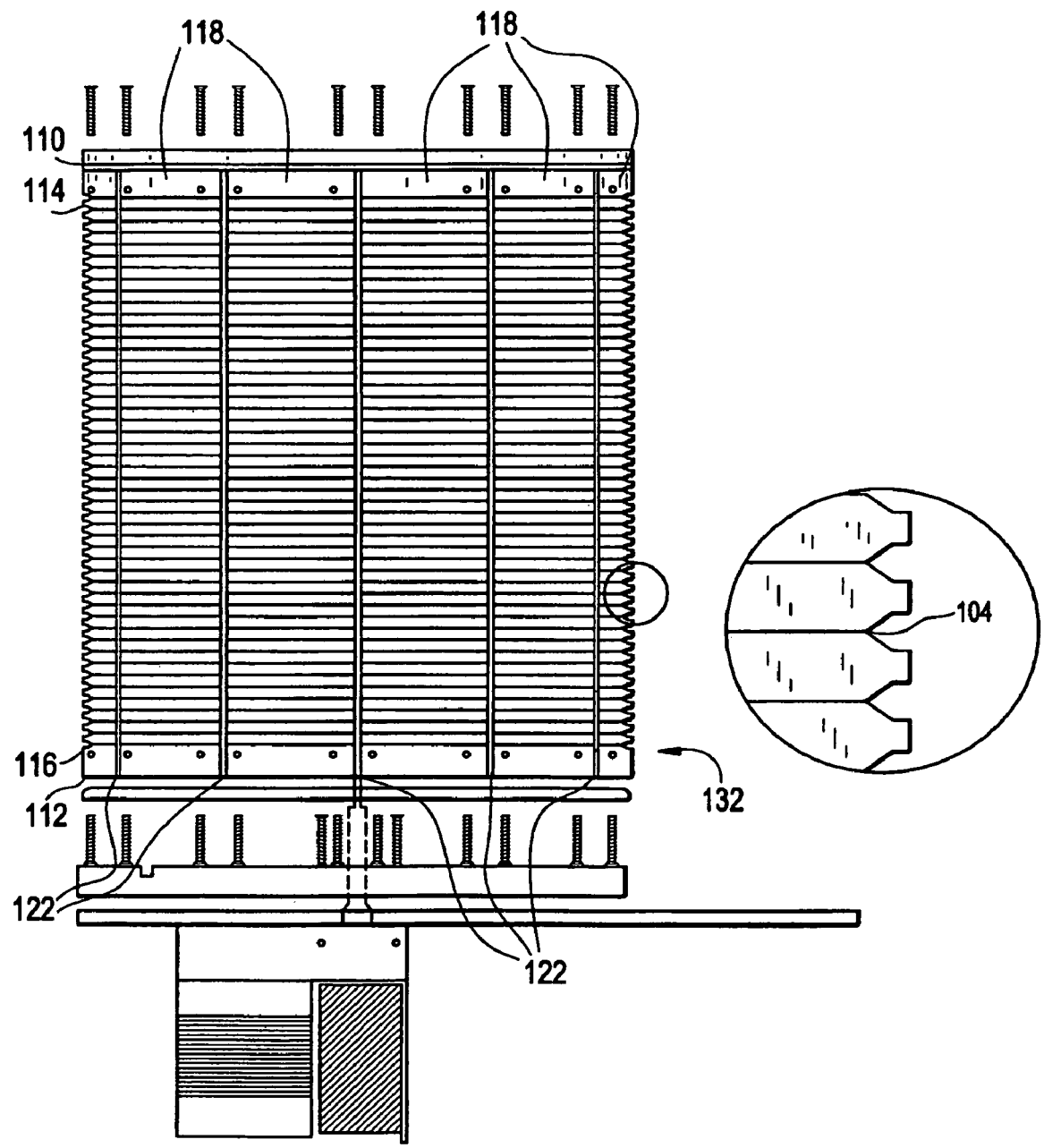
FIG. 9 is an elevation view of an alternate embodiment of the thermal cycle system of the present invention.
Figure 10:
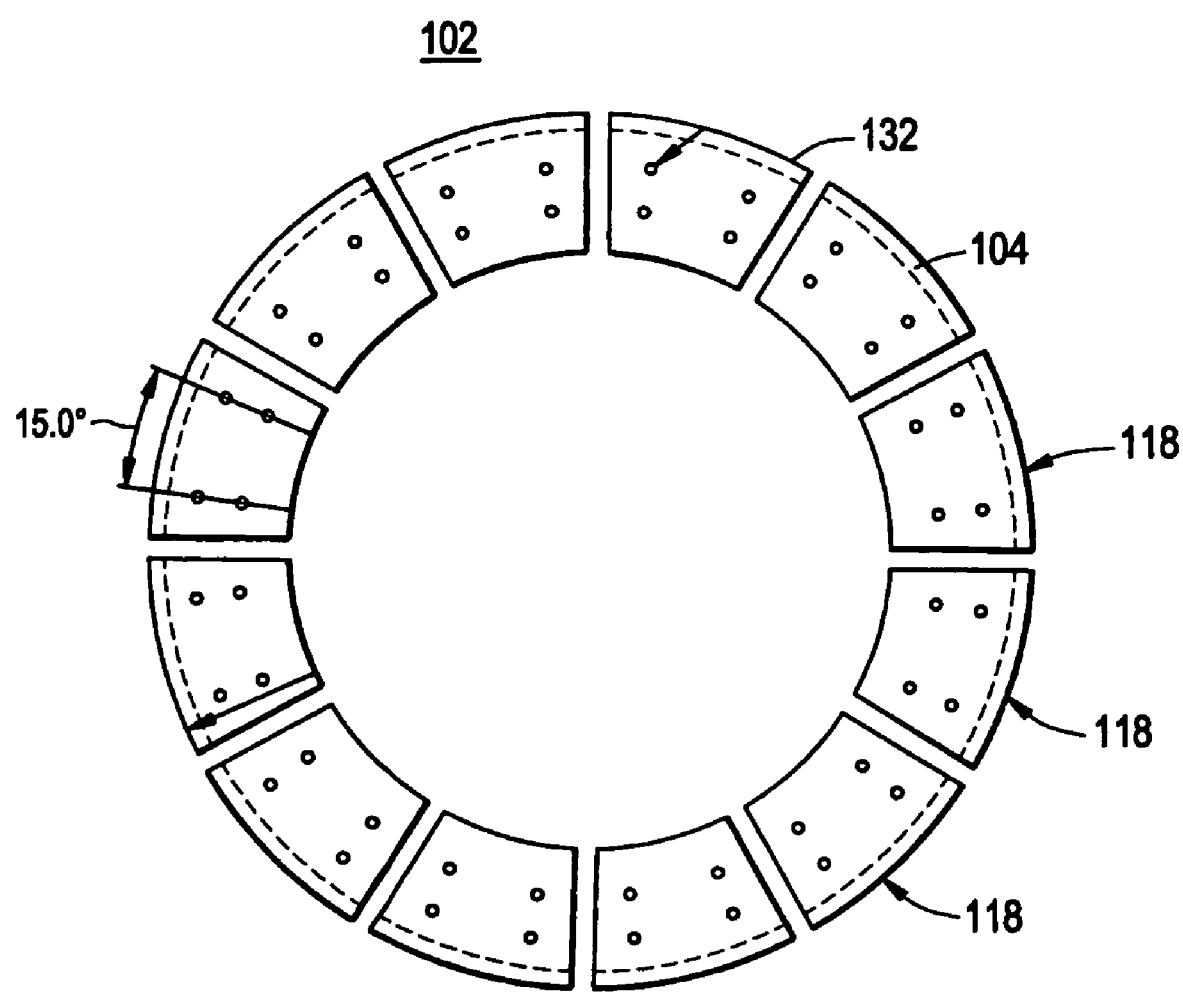
FIG. 10 is a top plan view of the thermal cycle system of FIG. 9.
Figure 11:
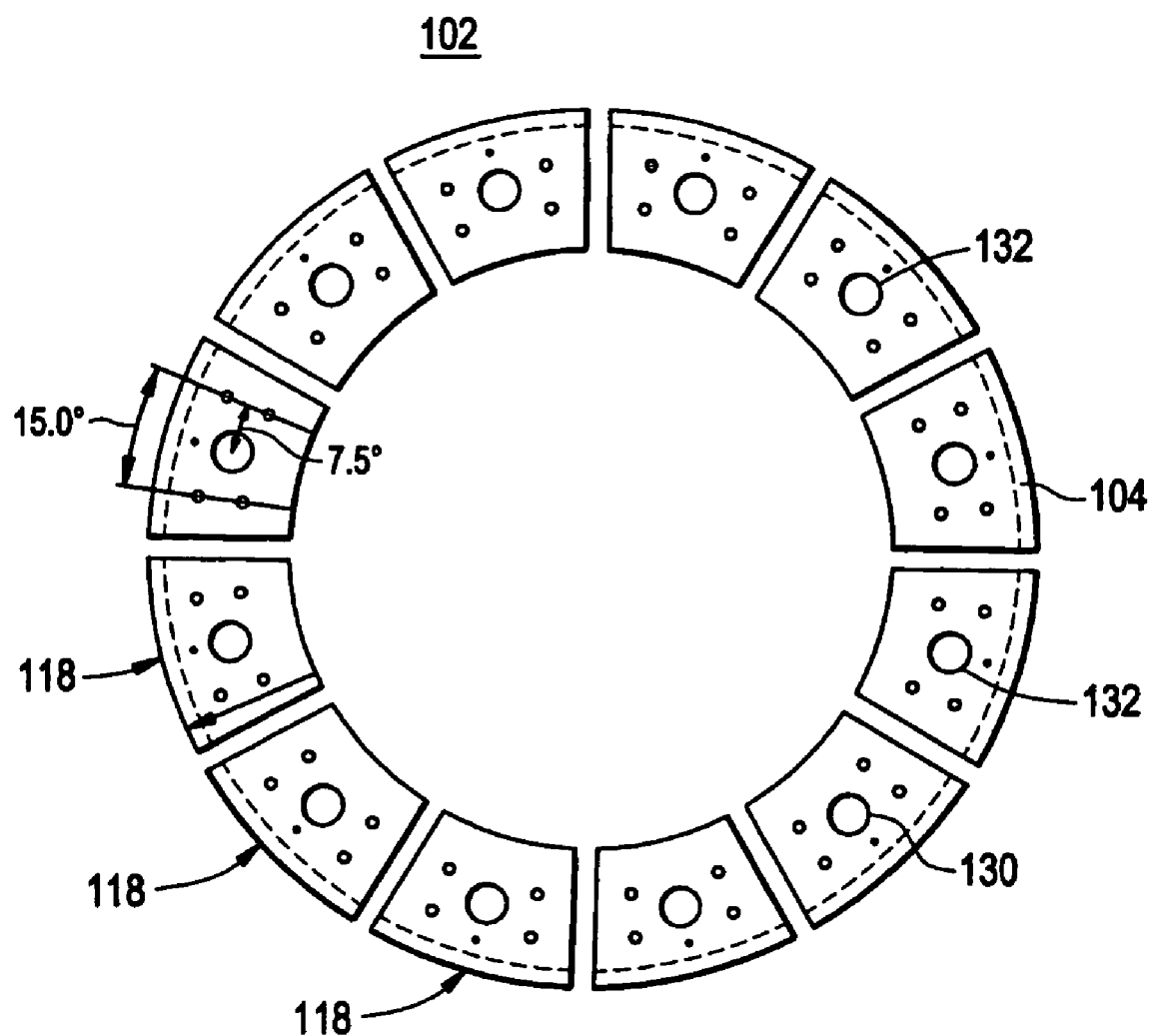
FIG. 11 is a bottom plan view of the thermal cycle system of FIG. 9.
Figure 12:
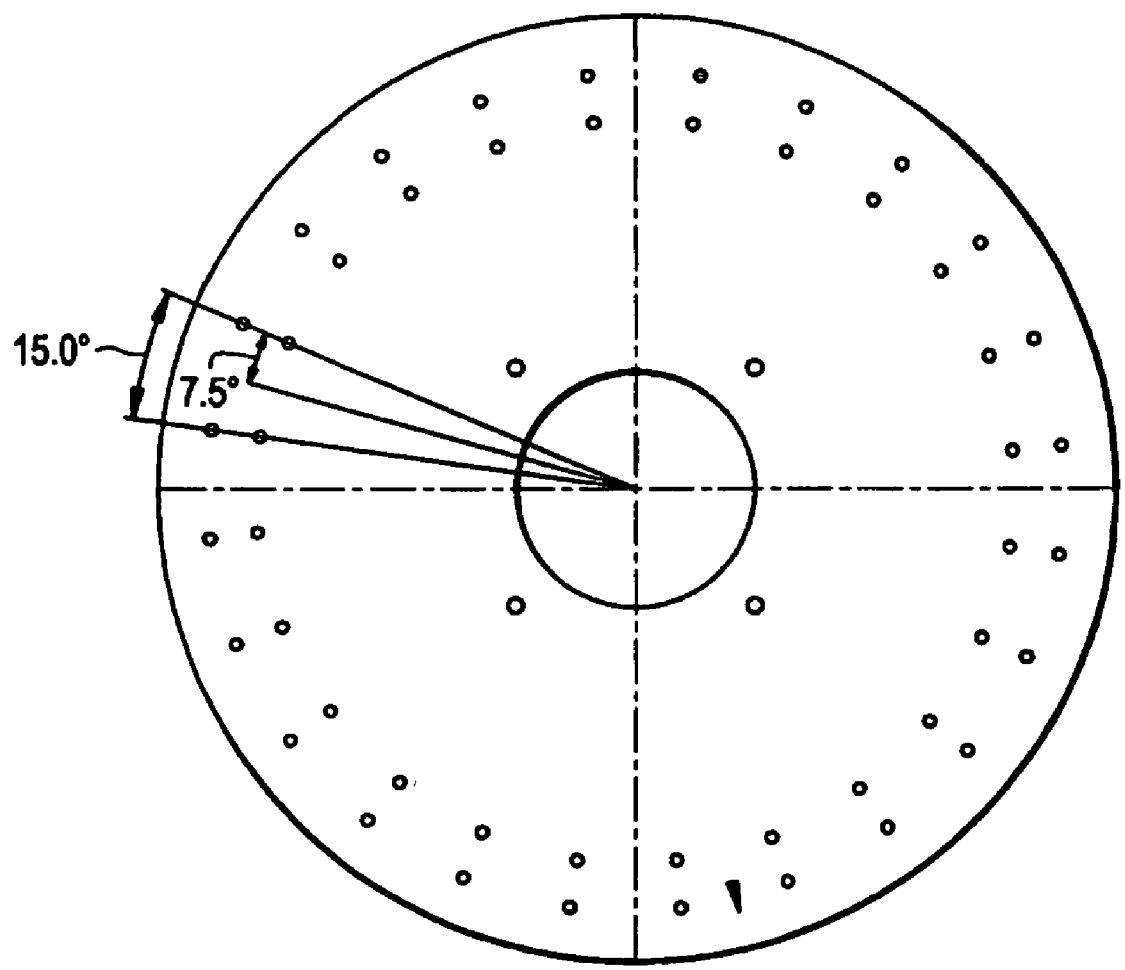
FIG. 12 is a plan view of a top cap of the thermal cycle system of FIG. 9.
Figure 13:
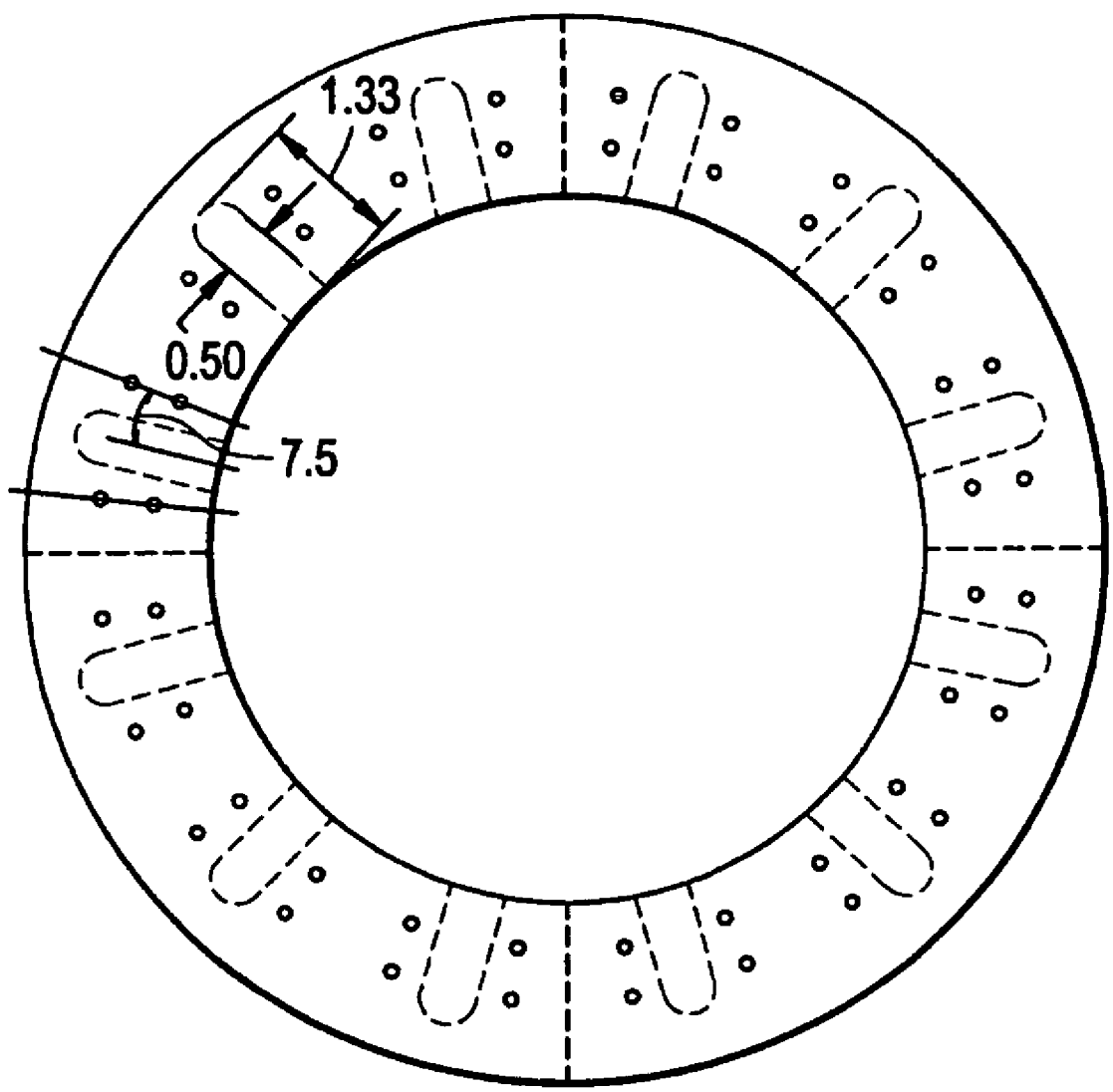
FIG. 13 is a plan view of a bottom cap of the thermal cycle system of FIG. 9.

Polymeric tubing to be used in the present invention include particularly a synthetic resinous fluorine-containing polymer tubing such as a flexible polytetrafluoroethylene (PTFE) or TEFLON brand of tubing. Suitable dimensions may be, for a circular cross-section, an outside diameter of about ⅛ inch so as to fit into channels 104 if such channel is about ⅛ inch in width. The tubing wall may be about 5/1000 inch and the inside diameter about 1/32 inch or more. For optional heat transfer, the inside diameter should be less than about ⅛ inch. The cross-section of the tubing may also be elliptical, square or rectangular. Suppliers include Zeus Industrial Products of Orangeburg, S.C. and Oxidation Systems Inc. of Fall River, Mass.

Surface absorbing polymers to be used in the present invention include those described in U.S. Pat. No. 6,709,692, particularly a block copolymer of ethylene oxide and propylene oxide, such as those provided by BASF of Florham Park, N.J. under the PLURONIC trademark. Examples include PLURONIC® F108, F108NF, F68 and F127.

The amount of surface absorbing polymer, such as a polyethylene oxide/polypropylene oxide block copolymer, can be in the range of about 1.5 milligrams per milliliter to 100 milligrams per milliliter. It is believed that the polymer acts to render the tubing surface more inert to the reactants than untreated tubing and also to protect the Taq enzyme from deactivation. This conclusion is reached in view of the observation that amplification is effectively inhibited after running PCR reagents without surface absorbing polymers through PFTE tubing of 20 inches or more. However, when the PCR reagents are collected from this tubing, they can be reactivated for DNA amplification in a conventional block thermalcycler by adding new Taq polymerase back to the reagents. This indicates the single critical component lost or inactivated by exposure to tubing is Taq DNA polymerase. When surface absorbing polymers are included in the mixture, the DNA amplification proceeds at the same or better levels than in a traditional block thermalcycler. Also, by pre-rinsing the tubing with an aqueous solution comprising about 1.5-3.5%

(w/v) of a surface blocking polymer (such as Pluronic F108) an amplification mixture which did not include the surface blocking polymer as a reagent could be used with successful amplification with less purification required at the end, although not as effectively as when the polymer was included as one of the PCR reagents. Also part of this invention is a method of conducting a polymerase chain reaction which comprises the steps of: (a) transporting an aqueous solution comprising a surface absorbing polymer through polymeric tubing followed by; (b) transporting a second aqueous solution comprising polymerase chain reactants through said tubing at temperatures sufficient to induce said polymerase chain reaction. The tubing utilized in the process of the invention is normally cleaned with a 10% bleach rinse and extensive washing with deionized water prior to switching the apparatus from the production of one particular DNA to another. While the cleaned tubing can be pre-treated with a wash of the surface absorbing polymer, such as Pluronic, prior to utilization of the apparatus for a further DNA synthesis, an advantage of the invention is the continual treatment and conditioning of the tubing during the reaction syntheses operation, thus lessening time spent in shut-down mode. Thus, the amount of polymer added is that sufficient to maintain conditioning of the tubing and protection of reaction enzyme(s) such as Taq from deactivation during DNA synthesis. This can be ascertained by observing the amount of polymer added to the reactant solution which turns the solution slightly cloudy. It is believed that this is the point at which micelles are produced around the Taq, i.e. an outer layer of polymer. This is to be contrasted with the use of oils and oil/water emulsion reactant systems.

Temperatures for the 3 steps of PCR when carried out according to the present invention are about 95° C., 57° C. and 72° C., respectively. However, the temperatures can be varied to increase specificity and yield of the reaction.

The present invention is directed to a method and composition for simultaneously maintaining multiple temperature regions within a single physical structure. The present invention is therefore particularly suited for use in the automated thermal cycling of substances, such as those used in the amplification of nucleic acid sequences. With reference to the drawings, and in particular to FIGS. 1-13, a thermal cycle system 100 of the present invention preferably comprises a temperature control body 102 having at least two sectors 118 and a path 104 that cyclically passes from one initial sector 118 to each successive sector 118 in turn, thereafter returning to the initial sector 118 and cyclically repeating passes from one sector 118 to the next sector 118 as many times as is desired. The path 104 traverses the sectors 118 by passing along an exterior surface 132 of the temperature control body 102 from one sector 118 to each successive sector 118, by boring through the sectors 118 internally from one sector 118 to each successive sector 118, or by a combination of such external or internal travel.

Each sector 118 comprises at least one means for changing or obtaining a temperature 120. The means for changing temperature 120 is capable of achieving and maintaining a specific desired temperature. The means for changing temperature 120 is therefore preferably a heater, cooler, Peltier device, heat pump, oven, firebox, thermal reaction chamber, or similar means. Each sector 118 is preferably substantially made of aluminum, aluminum alloy, metal, metal alloy, a thermal conductor, an asymmetric thermal conductor, or combination thereof. The means for changing temperature 120 thereby heats, cools or maintains the temperature of the sector 118 such that the section of the path 104 located in or on each sector 118 is similarly heated, cooled, or maintained at the particular temperature of that sector 118.

Each sector 118 is also preferably separated from other sectors 118 by a thermal barrier 122 located between the sectors 118. The thermal barrier 122 may be passive, and may comprise a thermal insulator, air, gas, liquid, solid, and/or a combination thereof. The thermal barrier 122 may alternatively or additionally be an active devise or material, such as a Peltier device, which can maintain a significant temperature differential. Each sector 118 therefore acts as an independent temperature sink wherein the means for changing temperature 120 for that sector 118 achieves and maintains a desired temperature throughout that sector 118, and a thermal barrier 122 thermally isolates each sector 118 from the other sectors 118. Multiple temperature regions are thereby efficiently achieved and maintained in a single body. An insulating layer 124 may optionally substantially surround the temperature control body 102 to minimize thermal transfer between the sectors 118 and the surrounding environment.

The temperature control body 102 may have any desirable shape, such as a cylinder, cone, triangle, rectangle, pyramid, polygon, block, or cube. The sectors 118 may also have any desired shape conforming to sections, parts, or pieces of the temperature control body 102. For example, the sectors 118 may be wedge shaped, arc shaped, or pie-sliced shaped, or may have the shape of sliced portions of a cylinder, cone, triangle, rectangle, pyramid, polygon, block, or cube. The sectors 118 may also be layered, one atop another. There may be any number of desired sectors 118. All the sectors 118 may be the same size, or one or more of the sectors 118 may be different size.

The thermal cycle system 100 also preferably comprises a plurality of temperature sensors 130. Each sector 118 preferably has one or more temperature sensors 130 located within or adjacent to that sector 118 to measure the temperature within that sector 118 or portion of sector 118. Each temperature sensor 130 produces temperature values output that directly or indirectly represents the temperature of that sector 118. Such temperature sensors 130 may be any conventional instrument for determining temperature. Such temperature sensors 130 may optionally be placed in or on the insulating layer 124.

The thermal cycle system 100 also preferably comprises a means for regulating temperature 134. The means for regulating temperature 134 regulates each means for changing temperature 120, such that desired temperatures within each sector 118 are achieved. Any number of means for regulating temperature 134 may be used to regulate the means for changing temperature 120. The mean for regulating temperature 134 preferably comprises a thermostat. In one embodiment, a computer system executing a software program is in communication with the means for changing temperature 120 and the temperature sensors 130, wherein the software uses a predefined set of target temperatures for each sector 118 for control and regulation of the means for changing temperature 120. The target temperatures are dictated by the desired application and use of the thermal cycle system 100, which in a preferred embodiment is PCR. The software receives the temperature values output from the temperature sensors 130. Each such temperature value represents directly or indirectly the temperature of a sector 118. The software compares the temperature value output of each sector 118 with its predefined target temperature for that sector 118. Then, if the temperature value output received from a temperature sensor 130 falls above or below a minimum predefined value, the software engages one or more of the means for changing temperature 120 in that sector 118 to increase or decrease the heat in that sector 118 or in an appropriate portion of that sector 118. That is, according to a temperature sensor's 130 value and position, the system may engage all or a subset of the means for changing temperature in the sector 118. Alternative means for regulating temperature 134 can be used such as any conventional thermostat system.

The thermal cycle system 100 also preferably comprises a means for moving 106 a fluid 128 along the path 104. The fluid 128 thereby cyclically passes from one sector 118 to another sector 118, and the temperature of the fluid 128 equilibrates with the temperature of the sector 118 through which or on which the fluid 128 is passing. The temperature of the fluid 128 thereby cyclically changes as it flows along the path 104. The fluid 128 preferably comprises any thermally dependent reaction mixture, reactants, or reagents. The fluid moving means 106 preferably comprises a pump, such as a peristaltic pump, a pressurized gas system, or similar means. For example, a pressurized helium system can be used to pump the fluid 128 along the path 104.

Pumps used to move the reactant mixture through the system include those of the peristaltic, cavity, centrifugal, piston, roots blowers, rotary vane, diaphragm, syringe and gear pump types. Syringe pumps are available from KD Scientific of Holliston, Mass. and generally are set up to provide a pulsitile continuous flow of liquid from a supply vessel through tubing and into the reaction zones without coming into contact with the syringes which power the movement of the liquid, the syringes coming into contact only with water which acts as the hydraulic fluid. For example, 2 syringes can be 180° out of phase so that as one is filling with water, the other empties its water to push reactant liquid into and through the DNA synthesis apparatus. An alternative pump which can come into contact with the reactant liquid is a rotary piston pump which uses a ceramic piston and cylinder which have no effect on the reactants. Examples include those supplied by IVEK Corporation of North Springfield, Vt.

In a particular embodiment of the thermal cycle system 100, the temperature control body 102 is a single substantially cylindrical body having a plurality of substantially pie-slice shaped or wedge-shaped sectors 118. The path 104 comprises a grooved channel circling or spiraling around the exterior surface 132 of the temperature control body 102. A length of tubing 126 is placed within or along the grooved channel. The desired temperature for each sector 118 is determined based upon the characteristics and requirements of a particular thermal-dependent reaction. The means for regulating temperature 134 and the means for changing temperature 120 are activated such that the desired temperature for each sector 118 is attained.

The temperature sensors 130 measure the actual temperatures of each sector 118, and each means for changing temperature 120 is activated or inactivated as appropriate to attain and maintain the desired temperature for each sector 118. The fluid moving means 106 moves or pumps the fluid 128 through the length of tubing 126. The fluid 128 is thereby subjected to a series of different temperature regions on a cyclical basis that ultimately results in a transformation or reaction of the fluid 128 into a product or products. The temperature control body 102 may optionally be attached to a base for support. A means for rotating the temperature control body 102 may also optionally be used to facilitate placing the length of tubing 126 within or along the grooved channel. Such means for rotating may comprise an electric motor with wheel and gear assemblies or similar alternative.

The thermal cycle system 100 is particularly suited for a large scale amplification of DNA via PCR. Thus, a particular embodiment of the thermal cycle system 100 has grooved channel path 104 circling around the exterior surface 132 of a single cylindrical temperature control body 102. Thus, the channel has a first end 114 near the top edge 110 of the temperature control body 102 and a second end 116 near the bottom edge 112 of the temperature control body 102. The depth of the groove is discretionary and may depend on the diameter of the length of tubing 126 that can be placed within or along the groove and/or may depend on the particular application of the thermal cycle system. The cylindrical temperature control body has twelve equally sized arc-shaped sectors 118, and each sector 118 has one means for changing temperature 120. Each sector 118 has one temperature sensor 130, specifically a type K thermocouple, internally placed within the sector 118. A fluid moving means 106, preferably a pressurized helium system, moves a fluid 128 through the length of tubing 126. The fluid 128 preferably comprises a DNA strand to be amplified, two primers, and a heat stable Taq polymerase. Additionally substances may be included in the fluid 128 to facilitate DNA amplification via PCR. A single means for regulating temperature 134 preferably regulates every means for changing temperature 120. The fluid moving means 106 moves the fluid 128 from sector 118 to sector 118 such that DNA amplification via PCR is optimized.

In one embodiment of the thermal cycle system 100, the cylindrical temperature control body 102 is divided into 3 equal pie-slice shaped sectors 118, and there are about 30 to about 40 "turns" of the channel around the cylinder with a particular number being about 33 turns. Each "turn" of the channel is a "cycle" of the fluid 128 traveling around the circumference of the exterior surface 132 of the cylinder. Also, tubing 126, e.g., PTFE tubing or TEFLON tubing or synthetic resinous fluorine-containing polymer tubing, within the channels is surrounded by 3 insulating layers 124 (one per sector 118), wherein each insulating layer 124 has eight temperature sensors 130. A peristaltic pump 106 is positioned about six to about seven inches from the point at which the tubing 126 extends away from the bottom 112 of the cylinder. Using this arrangement of the apparatus, the preferred method for using the present apparatus pumps the fluid 128 through the tubing 126 at a rate of about 45 seconds per section 118 (temperature zone), resulting in a flow rate of about 135 seconds per cycle (1 "turn" of the tubing 126 around the cylinder).

The temperature and cycle times imposed on the reagents by the sectors/temperature zones 118 are preferably consistent with the well-known and current process of PCR. The preferred use of the present apparatus and method for a continuous thermal cycle system is amplifying DNA, but this use of the present invention is for convenience purposes only. It would be readily apparent to one of ordinary skill in the relevant art to use the apparatus and method of the present invention in a different application requiring the continuous heating or cooling of a fluid 128 through multiple temperature zones.

The fluid 128 may be mixed or created in a large batch prior to its introduction into the length of tubing 126, or the fluid 128 may be created just-in-time or on-the-fly right before it is introduced into the length of tubing 126. The fluid 128 is preferably a substantially homogeneous temperature-dependent reaction mixture, and there is preferably a continuous supply of such fluid 128 through the length of tubing 126. A means of controlling the introduction of the fluid 128 may be used, such as a computer system and software program. The software program preferably uses a predefined protocol for determining the proper mix (by proportions), sequential order, and timing for inputting the fluid 128, and/or the fluid components, into the length of tubing 126. In one embodiment, the protocol for introducing the fluid 128 components is determined by particular PCR requirements. Any means for introduction of the fluid 128 may be used, such as a pump valve manifold or network known to those skilled in the art.

The resulting fluid 128 output from an end of the tubing is collected by conventional means. In a preferred embodiment, the resulting fluid contains amplified DNA. In addition, it is readily apparent that the apparatus and method of the present invention will provide a continual supply of amplified DNA so long as the pump is feeding the fluid components through the apparatus as described herein. The DNA may then be separated out from the reaction mixture, such as to remove the surface absorbing polymer, such as the block copolymer therefrom.

A method of the present invention for the facilitation of a chemical reaction requiring cyclical temperature changes therefore comprises activating a means for changing temperature 120 on a thermal cycle system 100 having a means for conveying a fluid such as a length of tubing 126 extending along a path 104, introducing a substantially homogenous temperature-dependent reaction mixture into the means for conveying, activating a means for moving 106 such that the reaction mixture moves through the means for conveying and such that the reaction mixture reacts to form a product, and collecting the product at an end of the means for conveying. The chemical reaction is preferably a polymerase chain reaction. The method optionally further comprises continuously replenishing the fluid at one end of the means for conveying.

An apparatus for continuously regulating temperature of a fluid, comprising: a cylinder comprising at least two sectors, an exterior surface, a top edge, a bottom edge, at least one temperature control means within each said sector, and a channel in said exterior surface, wherein said channel has a first end and a second end, and wherein said channel spirals around said exterior surface; a piece of tubing having a first end, a second end, and a length, said tubing positioned within said channel wherein said first end of said tubing extends from said first end of said channel and said second end of said tubing extends from said second end of said channel; a means for dispensing a fluid into said second end of said tubing; a means for moving in communication with said tubing wherein said moving means moves said fluid through said tubing from said second end of said tubing to said first end of said tubing; a means for determining a temperature of said tubing as said fluid flows through said tubing across each said sector of said cylinder; and a means for regulating said one or more temperature control means, wherein said means for regulating is in communication with said means for determining.

The apparatus wherein said first end of said channel terminates near said top edge of said cylinder and said second end of said channel terminates near said bottom edge of said cylinder.

A method for the facilitation of a chemical reaction requiring cyclical temperature changes, said method comprising the steps of: (a) activating means for changing temperature on a thermal cycle system, where said thermal cycle system comprises: a temperature control body comprising at least two sectors, an exterior surface, and a path cyclically passing through said sectors, and wherein each said sector comprises of at least one of said means for changing temperature; a means for conveying a fluid, wherein said means for conveying extends along said path; and a means for moving in communication with said means for conveying wherein said means for moving is adapted for moving said fluid through said means for conveying; (b) introducing a substantially homogeneous temperature-dependent reaction mixture into said means for conveying; (c) activating said means for moving such that said reaction mixture moves through said means for conveying, and such that said reaction mixture reacts to form a product; and (d) collecting said product at a first end of said means for conveying.

Figure 15:
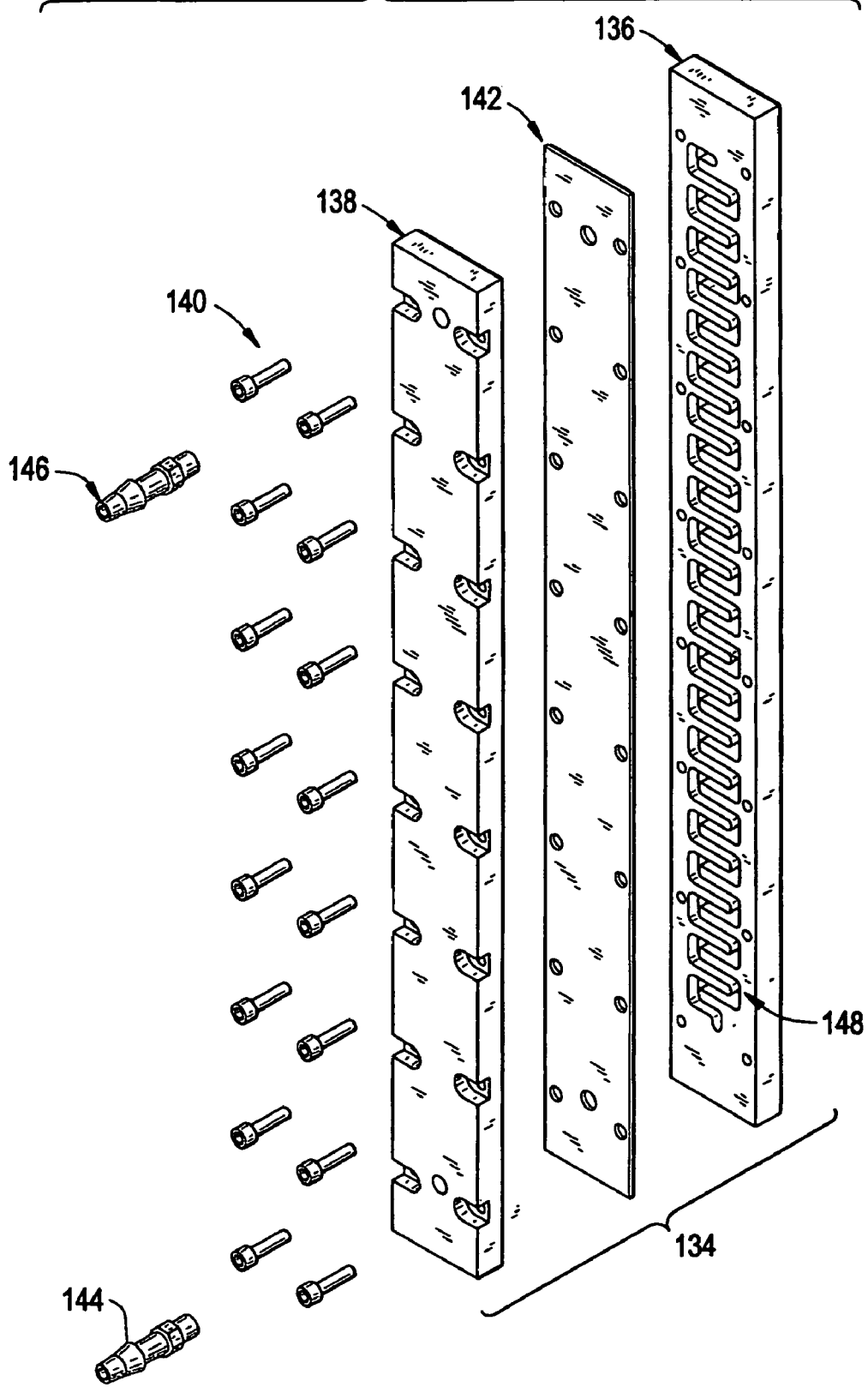
FIG. 15 is an exploded perspective view of a cooling module.
Figure 16:
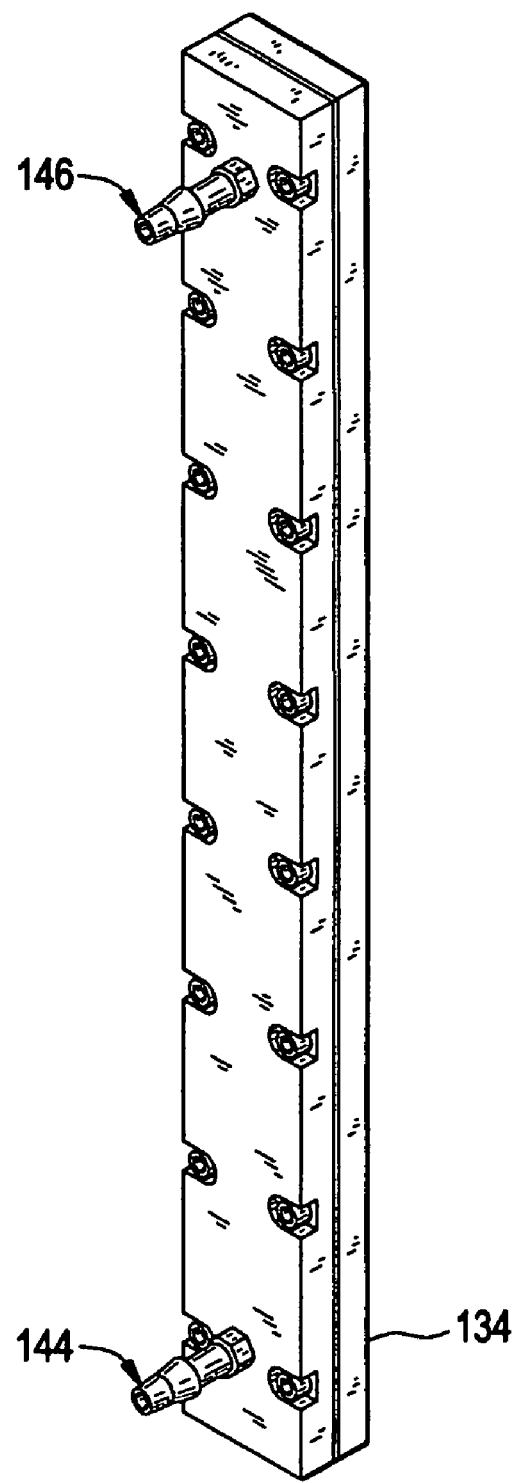
FIG. 16 is a closed perspective view of a cooling module.
Figure 17:
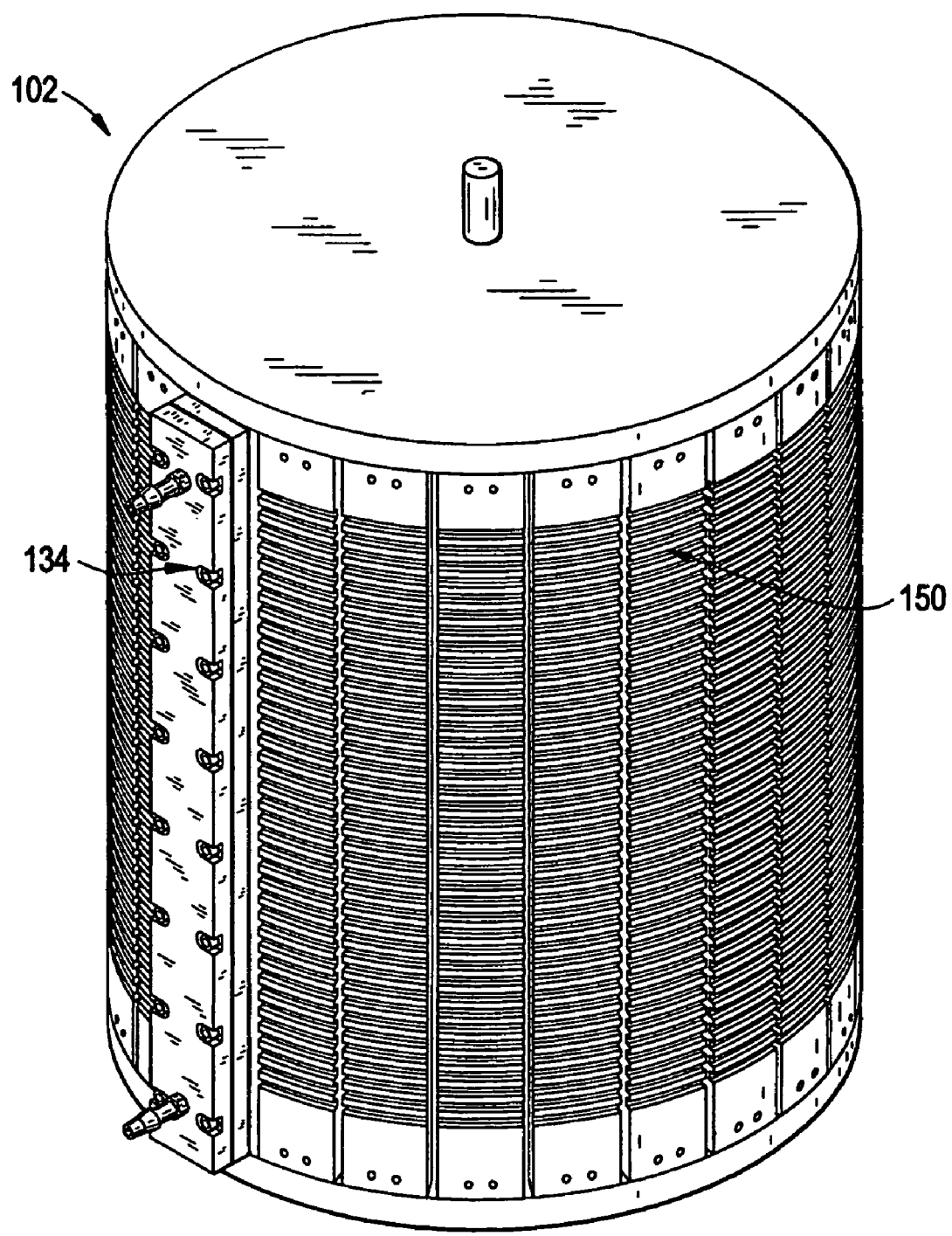
FIG. 17 is a perspective view of a cooling module connected to a thermal cycler.

A liquid cooling module which may be used in the invention may be as set forth in FIGS. 15, 16 and 17. The cooling module is an add-on device for a continuous PCR thermal cycler that increases the thermal load which can be placed on the thermal reaction cylinder of the thermal cycler, thereby increasing either the flow rate or volume of fluid contained therein to enable faster production of specific DNA structures. Through experiments conducted on an embodiment of this device, a temperature drop of up to 60° C. has been observed. This has enabled a four-fold increase in fluid volumes in the thermal cycler, which is equivalent to a four-fold production speed increase.

The liquid cooling module 134 consists of an aluminum module that is made up of two plates 136 and 138 that are screwed together with screws 140 and sealed with a gasket 142. An input and output port 144 and 146 are provided to allow liquid coolant to flow through the module 134. During operation, the module is affixed to the side of a heated cylinder temperature control body 102 that has threads around the outer surface and is divided into 24 sections 150 in a circular array. The temperature of each section may be set independently. The module 134 is the same width and height as one section. Tubing is wrapped around the cylinder through threads machined into the surface and the module is affixed to a section where a large temperature drop must occur. DNA reagents for PCR flow through the tubing which follows a helical path around the outside perimeter of the cylinder and are heated or cooled as they pass through each section. When the reagents reach the module, their heat is conducted into the cylinder section and outer surface of the module 134. When the reagents enter the next section, they are very close to the temperature of the section. To expel heat from the cylinder, the module has a serpentine channel 148 running through it that carries fluid coolant at a high flow rate. This serpentine design creates turbulent flow within the coolant, thereby increasing thermal transfer between the module and coolant. The coolant is expelled from the system through a port 146 once it has passed through the module. The coolant may be collected in a chiller to be cooled and passed again through the system or permanently expelled.

EXAMPLE 1

A sample was prepared containing: 12% $MgCl_2$ (25 mM), 0.33% Taq DNA polymerase (5 units/μl), 2.0% dNTP's (deoxyadenosine triphosphate (dATP), deoxycytidine triphosphate (dCTP), deoxyguanosine triphosphate (dGTP) and deothythimidine triphosphate (dTTP), 8.0% template (2 μg/ml), 61.66% Pluronic F108 solution (1.5% solution), 4% forward primer, 4% reverse primer, 8% reaction buffer (10× concentration). The solution can be scaled up to the correct volume using these figures. The twelve vertical sectors 118 of the cylindrical temperature control body 102 were heated to three different temperatures, four adjacent sectors 118 were heated to 95° C., another four adjacent sectors 118 were heated to 59° C., and the final four adjacent sectors 118 were heated to 72° C. 1/32" ID, 1/16" OD TEFLON PTFE tubing was wrapped around the temperature control body 102 thirty times to subject the length of tubing 126 and reaction mixture to the three different temperatures thirty different times in succession. The reaction mixture was them pumped through this tubing 126 using a pressurized vessel at 20 PSI. After the reaction mixture was fed to the temperature control body 102, mineral oil was used to push the sample through the entire length of tubing 126. The flow rate of the reaction mixture was controlled with a flow valve to 0.25 ml/min. The specific DNA sequence (whose limits are defined by the oligonucleotided primers) present in the sample was amplified as it passed cyclically through the temperature zones. After the thirtieth cycle, the tubing 126 exited the cylinder 102, and the contents were collected. The sample was analyzed on a Cambrex Reliant Precast 2% Agarose Gel and stained with ethidium bromide.

Figure 14:
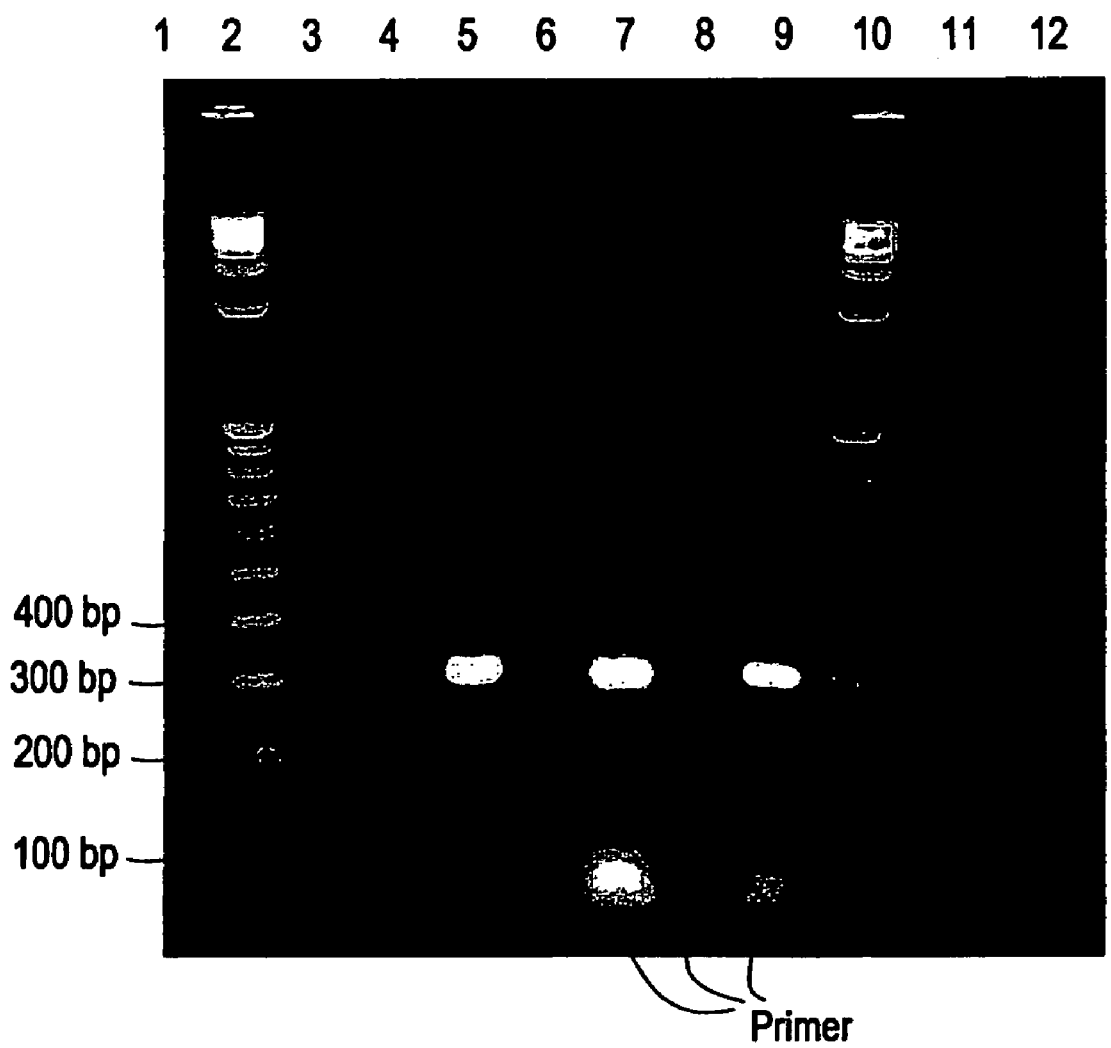
FIG. 14 is a photograph of an electrophoresis gel demonstrating the efficiency of an embodiment of the thermal cycle system of the present invention as compared with the efficiency of a conventional system.

An image of the gel was acquired using a BIORad Geldoc EQ systems and is shown in FIG. 14. The lane contents were as follows: lane 1 empty; lane 2 ladder; lane 3 no template negative control (sample A); lane 4 empty; lane 5 sample amplified in an embodiment of the thermal system 100 (sample B); lane 6 empty; lane 7 sample amplified in an embodiment of the thermal cycle system 100 followed by amplification in a conventional Perkin Elmer 480 machine (sample C); lane 8 empty; lane 9 positive control sample run with the conventional Perkin Elmer 480 machine (sample D); lane 10 ladder; lane 11 empty; and lane 12 empty.

The image was analyzed using ImageJ version 1.33u software wherein intensity data was extracted to obtain integrated intensities and calculations including background subtraction, and no other normalization. The band intensity for sample A was 0.07, the band intensity for sample B was 3.62, the band intensity for sample C was 3.77, and the band intensity for sample D was 3.19.

These data indicates that the systems and method of this invention is as efficient, if not more efficient, than an example of a standard commercial system, a Perkin Elmer 480 machine. Three identical reaction mixtures were prepared and one sample was examined in its unamplified form without template (sample A), one sample was run with the system of this invention (sample B), one sample was first run with the system of this invention and then run through a conventional commercial system (sample C), and one sample was run on a conventional commercial system (sample D). The intensity of the band on a gel at the targeted mass (300 bp) is an indicator of the quantity of DNA product produced.

Sample C produced the most intense band, but it is not very much more intense than the sample produced by this invention alone. Since sample C was subjected to thirty cycles with an embodiment of the thermal cycle system 100, then with thirty cycles of a commercial system, it is reasonable to expect some additional amplification if active reagents remain after exiting the machine used in the present invention.

Sample B, the DNA produced using the machine used in this invention, produced the second most intense band. Sample D is included to demonstrate the relative quantity of DNA to be expected from a conventional commercial system, the Perkin Elmer system. The band from the commercial system, sample D, is less intense than the band from this system and method of this invention sample B. This means that the system and method used in this invention is equal or better in efficiency than the commercial system. Sample A is used to indicate that no DNA (or a negligible amount of signal) is observed in a system subjected to amplification conditions (in the Perkin Elmer commercial system) but lacking template DNA, that there is not a contaminant in the reaction solution which could be misinterpreted as amplification. The important feature of this data is the fact that the sample B band is more intense (indicating a better reaction) than the same reaction carried out on the conventional system.

EXAMPLE 2

A reaction mixture with Pluronic is constructed by mixing 3% weight/volume Pluronic F127 with water and adding this to the PCR reaction mix, resulting in the following concentrations:

| Reagent | Concentration of Stock Solution | % of Final Solution |
| --- | --- | --- |
| MilliQ Water | | 79.9% |
| Pluronic F127 solution | Add 3% powder to water to dissolve, slightly increasing volume | 3% |
| PCR Buffer (matched to enzyme by manufacturer) | 10X | 10% |
| pGEM 3ZF+ plasmid | 5 milligram/milliliter | 0.06% |
| MgCl2 | 150 milliMolar | 2% |
| Primer forward CGATTTCGGCCTATTGGTTA (SEQ ID NO: 1) | 20 microMolar | 2% |
| Primer Reverse CGGTGAAAACCTCTGACACA (SEQ ID NO: 2) | 20 microMolar | 2% |
| Taq DNA polymerase | 5 units/microliter | 0.6% |
| Deoxynucleotide Mix | 10 micromole each nucleotide | 2% |
| | | 100% |

The PCR mixture is kept chilled before it is pumped through the machine and after collection. The machine uses thirty wraps of PFTE tubing with 1/16 inch ID and 1/8 inch OD. The PCR mix is made in volumes up to 500 ml and kept at 4 degrees Centigrade prior to cycling. The sectors of the machine are evenly divided into 12 sectors in this example. The first four sectors are heated to 95 degrees Centigrade, the next four sectors are heated to 58 degrees Centigrade and the final four sectors are heated to 72 degrees Centigrade. The flow rate of the pump was maintained such that the fluid passes through four sectors in 33 seconds for a total of 99 seconds per sequential wrap of tubing and a total time of 2970 seconds for the first of the solution to completely traverse the tubing.

EXAMPLE 3

A range of Pluronic concentrations are described using the same DNA template, oligonucleotide primers and temperature/flow concentrations as in Example 2 with a reaction mixture with Pluronic F108 that is constructed by mixing 1.5% weight/volume Pluronic F108 with water and adding this to the PCR reaction mixture with the amount of MilliQ water varying to bring the final volume to 100%.

| Reagent | Concentration of Stock Solution | % of Final Solution |
|---|---|---|
| MilliQ Water | | 64%-0% |
| Pluronic F108 | Add 1.5% powder to water to dissolve | 8%-72% |
| PCR Buffer (matched to enzyme by manufacturer) | 10X | 8% |
| pGEM 3ZF+ plasmid | 0.1 milligram/milliliter | 8% |
| MgCl2 | 25 milliMolar | 12% |
| Primer forward CGATTTCGGCCTATTGGTTA (SEQ ID NO: 1) | 10 microMolar | 4% |
| Primer Reverse CGGTGAAAACCTCTGACACA (SEQ ID NO: 2) | 10 microMolar | 4% |
| Taq DNA polymerase | 5 units/microliter | 0.33% |
| Deoxynucleotide Mix | 10 micromole each nucleotide | 2% |
| | | 100% |

The PCR mixture is kept chilled before it is pumped through the machine and after collection. The machine uses thirty wraps of PFTE tubing with 1/16 inch ID and 1/8 inch OD. PCR mix is made in volumes up to 50 ml and kept at 4 degrees Centigrade prior to cycling. The sectors of the machine are evenly divided into 12 sectors in this example. The first four sectors are heated to 95 degrees Centigrade, the next four sectors are heated to 58 degrees Centigrade and the final four sectors are heated to 72 degrees Centigrade. The flow rate of the pump was maintained such that the fluid passes through four sectors in 33 seconds for a total of 99 seconds per sequential wrap of tubing and a total time of 2970 seconds for the first of the solution to completely traverse the tubing.

EXAMPLE 4

This example describes use of 1 rinse of the tubing in the machine with 1.5% Pluronic solution for times ranging from 30 minutes to 60 minutes to pretreat the tubing followed by pumping the PCR reagent mixture which does not contain Pluronic or other surface absorbing polymer. This example used the same DNA template, oligonucleotide primers and temperature/flow concentrations in Example 2 under a reaction mix.

| Reagent | Concentration of Stock Solution | % of Final Solution |
|---|---|---|
| MilliQ Water | | 62%-0% |
| PCR Buffer (matched to enzyme by manufacturer) | 10X | 8% |
| pGEM 3ZF+ plasmid | 0.1 milligram/milliliter | 8% |
| MgCl2 | 25 milliMolar | 12% |
| Primer forward CGATTTCGGCCTATTGGTTA (SEQ ID NO: 1) | 10 microMolar | 4% |
| Primer Reverse CGGTGAAAACCTCTGACACA (SEQ ID NO: 2) | 10 microMolar | 4% |
| Taq DNA polymerase | 5 units/microliter | 0.33% |
| Deoxynucleotide Mix | 10 micromole each nucleotide | 2% |
| | | 100% |

The PCR mixture is kept chilled before it is pumped through the machine and after collection. The machine uses thirty wraps of PFTE tubing with 1/32 inch ID and 1/16 inch OD. PCR mix is made in volumes up to 10 ml and kept at 4 degrees Centigrade prior to cycling. The sectors of the machine are evenly divided into 12 sectors in this example. The first four sectors are heated to 95 degrees Centigrade, the next four sectors are heated to 58 degrees Centigrade and the final four sectors are heated to 72 degrees Centigrade. The flow rate of the pump was maintained such that the fluid passes through four sectors in 33 seconds for a total of 99 seconds per sequential wrap of tubing and a total time of 2970 seconds for the first of the solution to completely traverse the tubing.

EXAMPLE 5

A reaction mixture of 75 milliliters was constructed as below. The machine was preset to run at the following temperatures and times: 95 degrees Centigrade for 30 seconds, 56 degrees Centigrade for 30 seconds and 72 degrees for 45 seconds for a total of 36 cycles. The flow rate was 0.222813 ml/minutes. The PCR reaction mixture was prepared in a suitably sized polypropylene container and mixed by inversion without vortexing. An aliquot of 50 microliters was removed to be used as a no template control.

| Reagent | Concentration of Stock Solution | % of Final Solution |
|---|---|---|
| MilliQ Water | | 75.3% |
| PluronicF108 | 2.5% powder w/volume in MilliQ Water | 6% |
| PCR Buffer (Nature Technologies) | 10X | 10% |
| pGEM 3ZF+ plasmid pGEM 3ZF+ plasmid with a range of DNA inserts from none to 1200 BP | 100 ng/milliliter | 0.06% |
| MgCl2 | 25 milliMolar | 2% |
| Primer forward 5'AAAGGGAATAAGGGCGACAC3' (SEQ ID NO: 3) | 10 microMolar | 2% |

| Reagent | Concentration of Stock Solution | % of Final Solution |
|---|---|---|
| Primer Reverse 5'CCTGATGCGGTATTTTCTCC3' (SEQ ID NO: 4) | 10 microMolar | 2% |
| Taq DNA polymerase from Nature Technologies | 5 units/ microliter | 0.7% |
| Deoxynucleotide Mix | 10 micromole each nucleotide | 2% |
| | | 100% |

The PCR mixture was kept chilled before it was pumped through the machine and after collection. The machine used thirty-six wraps of PFTE tubing with 1/16 inch ID and 1/8 inch OD. The PCR mix was made in volumes up to 250 ml and kept at 4 degrees Centigrade prior to cycling. The sectors of the machine are evenly divided into 24 sectors in this example. The first six sectors are heated to 95 degrees Centigrade, the next six sectors are heated to 56 degrees Centigrade and the final 10 sectors are heated to 72 degrees Centigrade. The flow rate of the pump was maintained such that the fluid passes through 105 seconds per sequential wrap of tubing and a total time of 3780 seconds for the first of the solution to completely traverse the tubing. A cooling sector is applied to the first of the 6 sectors of the machine set to the 56 degrees Centigrade. Tap water was run through the cooling sector to dissipate heat and more quickly bring the solution from 95 degrees Centigrade to 56 degrees Centigrade. The machine's tubing is cleaned between uses with 10% Bleach or a commercial PCR cleaner such as Bleachrite and rinsed with MilliQ water between uses. The yield of 475 base pair DNA amplicon from this experiment was 1263 ug after the nucleotides and primers were removed from the sample by membrane filtration and ethanol precipitation.

What is claimed is:

1. A method of conducting a polymerase chain reaction which comprises transporting continuously a liquid through polymeric tubing disposed through a first reaction cycle region and at least a second reaction cycle region, each of which regions comprises at least a first temperature zone and a second temperature zone, the temperature in each zone of said at least second reaction cycle region being substantially identical to the corresponding first temperature zone and second temperature zone in said first reaction cycle region, wherein said liquid is an aqueous solution comprising polymerase chain reaction (PCR) reactants and a block copolymer of ethylene oxide and propylene oxide dissolved in said aqueous solution.

2. The method of claim 1, wherein said method comprises transporting said liquid through from about 10 to 40 reaction cycle regions, each of which reaction cycle regions comprises at least a first temperature zone and a second temperature zone, the temperature in each zone of said reaction cycle regions being substantially identical to the corresponding zone in said first reaction cycle region.

3. The method of claim 1, wherein said polymeric tubing is flexible polytetrafluoroethylene tubing.

4. The method of claim 1, wherein said liquid is transported into, through and out from said polymeric tubing without physical barriers therein.

5. The method of claim 1, wherein said liquid is a homogeneous aqueous solution.

6. The method of claim 1, wherein each of said reaction cycle regions comprises a first temperature zone, a second temperature zone and a third temperature zone.

7. The method of claim 6, wherein the temperature in said first temperature zone is about 94-96° C., the temperature in said second temperature zone is about 55-60° C. and the temperature in said third temperature zone is about 70-73° C.

8. The method of claim 7 wherein the temperature in said first temperature zone is about 95° C., the temperature in said second temperature zone is about 57° C. and the temperature in said third temperature zone is about 72° C.

9. The method of claim 1 wherein said PCR reactants include Taq DNA polymerase and the concentration of said block copolymer is sufficient to protect said Taq DNA polymerase from deactivation.

10. The method of claim 1 wherein said PCR reactants include Taq DNA polymerase and the concentration of said block copolymer is sufficient to protect said Taq DNA polymerase from deactivation.

11. The method of claim 1 wherein the concentration of said block copolymer is about 1.5 mg/ml to about 100 mg/ml.

12. A method of conducting a polymerase chain reaction which comprises the steps of:
    a. transporting an aqueous solution comprising a block copolymer of ethylene oxide and propylene oxide through polymeric tubing followed by;
    b. transporting continuously a second aqueous solution comprising PCR reactants through said tubing at temperatures sufficient to induce said polymerase chain reaction.

13. A method of conducting a polymerase chain reaction, which comprises transporting continuously a liquid through polymeric tubing disposed through from about 10 to about 40 reaction cycle regions, each of which reaction cycle regions comprises a first temperature zone, a second temperature zone and a third temperature zone, the temperature in each zone of a reaction cycle region being substantially identical to the corresponding zone in the other reaction cycle regions, wherein said liquid is a homogeneous aqueous solution comprising PCR reactants and a block copolymer of ethylene oxide and propylene oxide dissolved in said aqueous solution.

14. The method of claim 13 wherein the temperature in said first temperature zone is about 94-96° C., the temperature in said second temperature zone is about 55-60° C. and the temperature in said third temperature zone is about 70-73° C. and the concentration of said block copolymer is about 1.5 mg/ml to about 100 mg/ml.

15. The method of claim 14 wherein the temperature in said first temperature zone is about 95° C., the temperature in said second temperature zone is about 57° C. and the temperature in said third temperature zone is about 72° C.

16. The method of claim 14 wherein said liquid is transported into, through and out from said polymeric tubing without physical barriers therein.

17. The method of claim 16 wherein said polymeric tubing is flexible polytetrafluoroethylene tubing.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgatttcggc ctattggtta                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cggtgaaaac ctctgacaca                                                   20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aaagggaata agggcgacac                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cctgatgcgg tattttctcc                                                   20